United States Patent
Weers et al.

(10) Patent No.: US 11,491,161 B2
(45) Date of Patent: *Nov. 8, 2022

(54) METHODS AND COMPOSITIONS FOR TREATMENT OF PULMONARY HYPERTENSION AND OTHER LUNG DISORDERS

(71) Applicant: Respira Therapeutics, Inc., Albuquerque, NM (US)

(72) Inventors: Jeffry Weers, Half Moon Bay, CA (US); Alain Romero, Brisbane, CA (US); Hugh Smyth, West Lake Hills, TX (US); Robert Curtis, Santa Fe, NM (US); Adaani Frost, Houston, TX (US); Zhen Xu, Rockville, MD (US); Revati Shreeniwas, Palo Alto, CA (US); Martin Donovan, Austin, TX (US)

(73) Assignee: Respira Therapeutics, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/534,282

(22) Filed: Nov. 23, 2021

(65) Prior Publication Data
US 2022/0079949 A1 Mar. 17, 2022

Related U.S. Application Data

(63) Continuation of application No. 17/146,173, filed on Jan. 11, 2021, which is a continuation of application No. 16/469,524, filed as application No. PCT/US2017/066519 on Dec. 14, 2017, now Pat. No. 10,912,778.

(60) Provisional application No. 62/434,185, filed on Dec. 14, 2016.

(51) Int. Cl.
| | |
|---|---|
| *A61K 31/53* | (2006.01) |
| *A61P 9/12* | (2006.01) |
| *A61K 9/00* | (2006.01) |
| *A61K 9/16* | (2006.01) |
| *A61K 31/192* | (2006.01) |
| *A61K 31/506* | (2006.01) |

(52) U.S. Cl.
CPC .............. *A61K 31/53* (2013.01); *A61K 9/008* (2013.01); *A61K 9/0075* (2013.01); *A61K 9/1623* (2013.01); *A61K 31/192* (2013.01); *A61K 31/506* (2013.01); *A61P 9/12* (2018.01)

(58) Field of Classification Search
None
See application file for complete search history.

(56) References Cited

U.S. PATENT DOCUMENTS

| | | | |
|---|---|---|---|
| 8,758,824 | B2 | 6/2014 | Lipp et al. |
| 9,339,507 | B2 | 5/2016 | Olschewski et al. |
| 10,912,778 | B2 | 2/2021 | Weers et al. |
| 2004/0077624 | A1 | 4/2004 | Fox et al. |
| 2007/0031349 | A1 | 2/2007 | Monteith et al. |
| 2009/0196930 | A1 | 8/2009 | Surber et al. |
| 2013/0213397 | A1 | 8/2013 | Curtis et al. |

FOREIGN PATENT DOCUMENTS

| | | |
|---|---|---|
| EA | 006154 B1 | 10/2005 |
| RU | 2571284 C2 | 12/2015 |
| WO | WO 2005/018624 A2 | 3/2005 |
| WO | WO 2007/134292 A2 | 11/2007 |
| WO | WO 2009/115235 A1 | 9/2009 |
| WO | WO 2011/030351 A2 | 3/2011 |
| WO | WO 2015/089105 A1 | 6/2015 |
| WO | WO 2016/114993 A1 | 7/2016 |

OTHER PUBLICATIONS

Blount, et al., "Binding of Tritiated Sildenafil, Tadalafil, or Vardenafil to the Phosphodiesterase-5 Catalytic Site Displays Potency, Specificity, Heterogeneity, and cGMP Stimulation," Molecular Pharmacology vol. 66, No. 1, 2004, 9 pages.
Center for Drug Evaluation and Research (CDER), U.S. Food and Drug Administation (FDA). *The Voice of the Patient: Pulmonary Arterial Hypertension*; Report date: Dec. 2014, 24 pages.
Corbin et al., "High Lung PDE5: A Strong Basis for Treating Pulmonary Hypertension with PDE5 Inhibitors", Biochemical and Biophysical Research Communications, vol. 334, No. 3, Sep. 2, 2005, pp. 930-938.
Corbin et al., "Vardenafil: Structural Basis for Higher Potency over Sildenafil in Inhibiting cGMP specific Phosphodiesterase-5 (PDE5)", Neurochemistry International, vol. 45, No. 6, Nov. 2004, pp. 859-863.
De Tejada , "Vardenafil Duration of Action", European Association of Urology, vol. 50, No. 5,Nov. 2006, pp. 901-902.

(Continued)

*Primary Examiner* — Nannette Holloman
(74) *Attorney, Agent, or Firm* — Haug Partners LLP

(57) ABSTRACT

Provided herein are methods for treating pulmonary hypertension. The methods include administering to a subject in need thereof an effective amount of a vasodilator, wherein the vasodilator is administered to the subject via inhalation pro re nata using a portable inhaler. In some embodiments, the vasodilator is a PDE5 inhibitor. Pharmaceutical compositions for pro re nata administration of vasodilators are also described.

30 Claims, 3 Drawing Sheets

(56) References Cited

OTHER PUBLICATIONS

Daoud F S et al: "Isoproterenol as a potential pulmonary vasodilator in primary pulmonary hypertension", American Journal of Cardiology, Cahners Publishing Co., Newton, MA, US, vol. 42, No. 5, Nov. 1, 1978 (Nov. 1, 1978), pp. 817-822, XP026341656, ISSN: 0002-9149 [retrieved on Nov. 1, 1978] p. 820, right-hand column, last paragraph.

Enderle et al., "Simultaneous quantification of endothelin receptor antagonists and phosphodiesterase 5 inhibitors currently used in pulmonary arterial hypertension." *Journal of Pharmaceutical and Biomedical Analysis*, 143(2017) 291-298.

Full Prescribing Information (label): Tyvaso™ (treprostinil) inhalation solution. Revised: Jul. 2009, 16 pages.

Ghofrani, et al., "Differences in Hemodynamic and Oxygenation Responses to Three Different Phosphodiesteraase-5 Inhibitors in Patients with Pulmonary Arterial Hypertension," Journal of the American College of Cardiology, vol. 44, No. 7, 2004, DOI: 10.1016/j.jacc.2004.06.060, 9 pages.

Hossein-Ardeschir Ghofrani, et al., "The role of combination therapy in managing pulmonary arterial hypertension," Eur Respir Rev 2014; 23: 469-475, DOI 10.1183/09059180.00007314, 7 pages.

Hsu Andrew R et al: 11 Sildenafil improves cardiac output and exercise performance during acute hypoxia, but not normoxia, Journal of Applied Physiology, American Physiological Society, US, vol. 100, No. 6, Jun. 1, 2006 (Jun. 1, 2006), pp. 2031-2040, XP009503977, ISSN:8750-7587, DOI: 10.1152/JAPPLPHYSIOL. 00806.2005 abstract.

International Search Report and Written Opinion dated Mar. 20, 2018 in related PCT application No. PCT/US2017/066519, 17 pgs.

Joachim Mittendorf et al: Discovery of Riociguat (BAY 63-2521): A Potent, Oral Stimulator of Soluble Guanylate Cyclase forthe Treatment of Pulmonary Hypertension 11, Hemmedchem, Wiley-VCH, vol. 4, No. 5, May 11, 2009 (May 11, 2009), pp. 853-865, XP002622814, ISSN: 1860-7179, DOI: 10.1002/CMDC. 200900014.

Mehrotra, et al., "The role of pharmacokinetics and pharmacodynamics in phosphodiesterase-5 inhibitor therapy," International Journal of Impotence Research (2007) 19, pp. 253-264.

Meis T et al: "Pulmonary hypertension: Role of combination therapy", Current Vascular Pharmacology, Bentham Science Publisher, Ilversum, NL, vol. 9, No. 4, Jun. 30, 2011 (Jun. 30, 2011), pp. 457-464, XP009503951, ISSN: 1570-1611, DOI: 10.2174/ 157016111796197242.

*Orange Book: Approved Drug Products with Therapeutic Equivalence Evaluations.* Patent and Exclusivity for: N022387, Treprostinil (Tyvaso). Retrieved from accessdata.fda.gov on Nov. 20, 2020, 2 pages.

Patel R et al: "Treatment of Pulmonary Hypertension", Medical Science Monitor, Mediscience Publikacje Naukowe, Warzaw, PL, vol. 18, No. 4, Jan. 1, 2012 (Jan. 1, 2012), pp. RA31-RA39, XP009503950, ISSN: 1234-1010, p. RA34, right-hand column, paragraph 4.

Weers, et al., "Formulation Design of Dry Powders for Inhalation", Novartis Pharmaceuticals Corporation, San Carlos, CA 94070, Published online Aug. 21, 2015 in Wiley Online Library (wileyonlinelibrary.com). DOI 10.1002/jps.24574, 30 pages.

Search Report dated Mar. 17, 2021 issued in the corresponding Russian application No. 2019121646/04.

Office Action dated Mar. 17, 2021 issued in the corresponding Russian application No. 2019121646/04 and its English translation. English Translation of the Office Action dated Jan. 11, 2022 issued in the corresponding Japanese application No. 2019-531750.

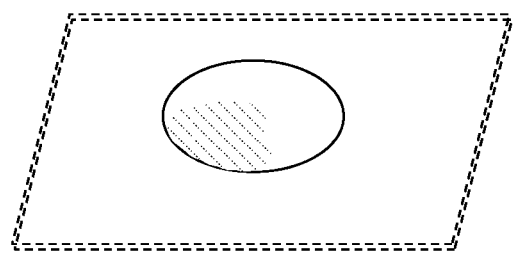
FIG. 3A
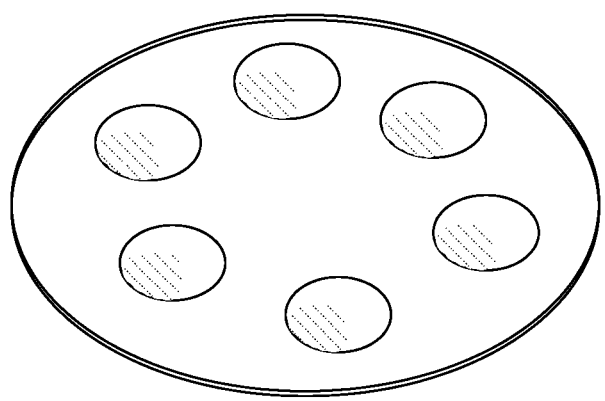
FIG. 3B
FIG. 3C
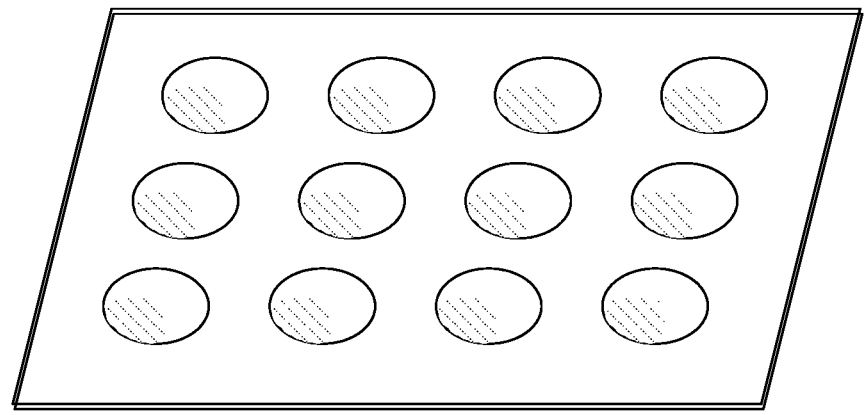

METHODS AND COMPOSITIONS FOR TREATMENT OF PULMONARY HYPERTENSION AND OTHER LUNG DISORDERS

CROSS REFERENCES TO RELATED APPLICATIONS

The present application is a continuation of U.S. patent application Ser. No. 17/146,173, filed on Jan. 11, 2021, which is a continuation of U.S. patent application Ser. No. 16/469,524, filed on Jun. 13, 2019, which is a U.S. National Stage Application of PCT International Application No. PCT/US2017/066519, filed on Dec. 14, 2017, which claims priority to U.S. Provisional Pat. Appl. No. 62/434,185, filed on Dec. 14, 2016, which are incorporated herein by reference in their entireties.

FIELD

The invention is related to methods and compositions for the treatment of pulmonary hypertension and other lung disorders.

BACKGROUND

The World Health Organization (WHO) has classified patients with pulmonary hypertension (defined as an average pulmonary artery pressure above 25 mm Hg at rest or over 30 mm Hg during exercise) into 5 groups, depending on the etiology of the disease. WHO Group 1—Pulmonary arterial hypertension (PAH) is a chronic disease characterized by proliferation and remodeling of vascular endothelial and smooth muscle cells in the small pulmonary arteries and arterioles. This results in a physical narrowing of the arteries, and progressive increases in pulmonary vascular resistance, elevation in pulmonary artery pressure, right heart failure, and eventually, death. The most commonly reported symptoms for PAH patients are dyspnea, fatigue, weakness, and a low exercise capacity. Patients are further categorized into one of four functional classes depending on the severity of their disease. WHO Class I patients exhibit no symptoms with ordinary activities. WHO Class II patients exhibit no symptoms at rest, but are uncomfortable or short of breath with ordinary activity such as climbing stairs, grocery shopping, or making the bed. WHO Class III patients may not have symptoms at rest, but their activities are greatly limited by shortness of breath, fatigue or near fainting. Patients in this class have difficulty in doing normal daily activities. Finally, WHO Class IV patients have symptoms at rest, and severe symptoms with any activity.

Currently, therapeutic options for PAH are oral, inhaled, or continuously administered intravenous or subcutaneous vasodilator therapies. All of the current PAH treatments are maintenance therapies, taken according to a specified treatment regimen, with treatment-related outcomes measured for product labeling over periods of chronic use of twelve weeks or longer.

Oral therapies for PAH include vasodilator drugs such as phosphodiesterase-5 enzyme inhibitors (PDE5i), endothelin receptor antagonists, prostacyclin analogs and prostacyclin receptor agonists, and soluble guanylate cyclase stimulators (sGCS). Current treatment regimens require oral administration of these active agents from one to three times daily.

Chronic infusion therapies for PAH are used principally in patients with continued or advancing WHO Class III or WHO Class IV symptoms. Intravenous therapies require placement of a chronic intravenous catheter, which has the attendant risks of drug delivery interruption and, most importantly, infection. Subcutaneous infusion of these drugs is frequently associated with substantial swelling, occasional localized infections, and, frequently, substantial local site pain. Both subcutaneous and intravenous methods require a continuously infusing pump that the patient must carry (e.g., from the size of a deck of cards to the size of a paperback book). Parenterally administered prostacyclins generally have significant systemic side effects. Though they target the pulmonary blood vessels, they also dilate arterial blood vessels throughout the body, resulting in systemic hypotension.

Though PAH is a disease of the pulmonary vascular bed, the only approved inhalation therapies are inhaled prostacyclin analogs which are prescribed as add-on maintenance therapy for patients who have not reached their treatment goals, but who have not deteriorated to the point of requiring infusion treatment. Alternatively, inhaled prostacyclin analogues are used for more severe patients who are unable to tolerate parenteral therapy. Due to their rapid clearance current treatment regimens for inhaled prostacyclin analogs require administration four to nine times daily. The complexity of the nebulizers used to deliver the drugs further contributes to their large treatment burden.

Although not used extensively today, vasodilators may also have utility in the treatment of other forms of pulmonary hypertension (PH), especially for those patients in WHO Group 3 PH or Group 4 PH. WHO Group 3 PH comprises patients with obstructive or interstitial lung diseases and/or hypoxemia. This includes patients with chronic obstructive pulmonary disease (COPD) and idiopathic pulmonary fibrosis (IPF). WHO Group 4 comprises PH patients with chronic thromboembolic PH (CTEPH).

Oral and parenteral vasodilators are used very cautiously in WHO Group 3 PH patients, and to date none of the vasodilators have been approved for use in these indications. One concern is that oral or parenteral administration of vasodilators in WHO Group 3 PH patients may lead to ventilation-perfusion mismatches and hypoxemia, ultimately leading to tissue hypoxia. With that said, although the cause of death for these patients is their primary respiratory disease, their exercise effort limitation and quality of life impairment are generally thought to be related to the hemodynamic compromise and increased pulmonary vascular resistance that is the hallmark of their disease.

Until recently, no PAH specific medications such as those described above were approved for use in WHO Group 4 patients with CTEPH. Riociguat (ADEMPAS®), an oral soluble guanylate cyclase activator/stimulator has now been approved for use in WHO Group 4 patients and WHO Group 1 patients.

PH severely affects a patient's day-day functioning, and has a devastating impact on their quality of life (QoL). According to patients, the symptoms of PH make it increasingly difficult to participate in household activities, or to hold a job outside the home. Tasks that were once easy (e.g., climbing stairs, exercising, cleaning the house) become more difficult and often leave them 'breathless'. Patients feel a loss in independence and purpose. Many fear being alone and without help, and of experiencing PH symptoms in public. These factors often negatively impact on their personal relationships. Aside from the impact of the disease, the adverse events and burden of current treatment options also negatively impact patient QoL. Despite being treated with maintenance therapies, including but not limited to various vasodilators such as listed above, many PH patients experience a "sundowning" phenomenon during the day as drug activity wears off, where performing routine functions that require physical exertion becomes difficult. This also negatively impacts patients' quality of life.

There are currently no medications approved by FDA for the treatment of PH that can be used on as needed basis (referred to as pro re nata (PRN), meaning as circumstances arise or dictate). In addition, current inhaled and IV delivery devices for delivering PH therapies are not convenient for the patient to use nor, as previously explained, are they readily portable.

BRIEF SUMMARY

Provided herein are methods and compositions that meet the significant need for treatments which acutely improve exercise tolerance and reduce symptoms, allowing PH patients to function more normally in their day to day lives. The methods and compositions address pervasive symptoms of PH, while reducing or eliminating drawbacks frequently cited by PH patients in conjunction with current therapies— the methods and compositions provided herein are less invasive than previous therapies, have a more convenient dosing schedule, and cause fewer sides effects.

Provided herein are methods for treating pulmonary hypertension. The methods include administering to a subject in need thereof an effective amount of a vasodilator, wherein the vasodilator is administered to the subject via inhalation on an as-needed basis (i.e., pro re nata or PRN) using a portable inhaler. The vasodilator can be administered in a powder composition. In some embodiments, the vasodilator is a PDE5 inhibitor. The methods can be used as an add-on to background oral therapy. The PRN vasodilator is intended for the acute treatment of PH as needed, to provide improvements in tolerance to exercise and activities of daily living. The methods provided herein improve patients' ability and capacity to satisfy their needs, which contributes significantly to improvements in patient-reported quality of life.

In a related aspect, a pharmaceutical carrier-based composition comprising a PDE5 inhibitor is provided. The composition contains a) at least about 0.1% of the PDE5 inhibitor, or a pharmaceutically acceptable salt or ester thereof, by weight relative to the total weight of the overall composition, and b) a powder base. In some embodiments, the carrier comprises crystalline lactose and an optional force control agent. Compositions wherein fine particle fraction on Stage 4 to filter of a Next Generation Impactor ($FPF_{S4-F}$/ED) is greater than 25% of the emitted dose are particularly advantageous for targeting to the pulmonary arteries, as explained herein.

BRIEF DESCRIPTION OF THE DRAWINGS

FIG. 3A-3C show exemplary blister packs for packaging formulations according to certain embodiments of the present disclosure.

DETAILED DESCRIPTION

Figure 1:
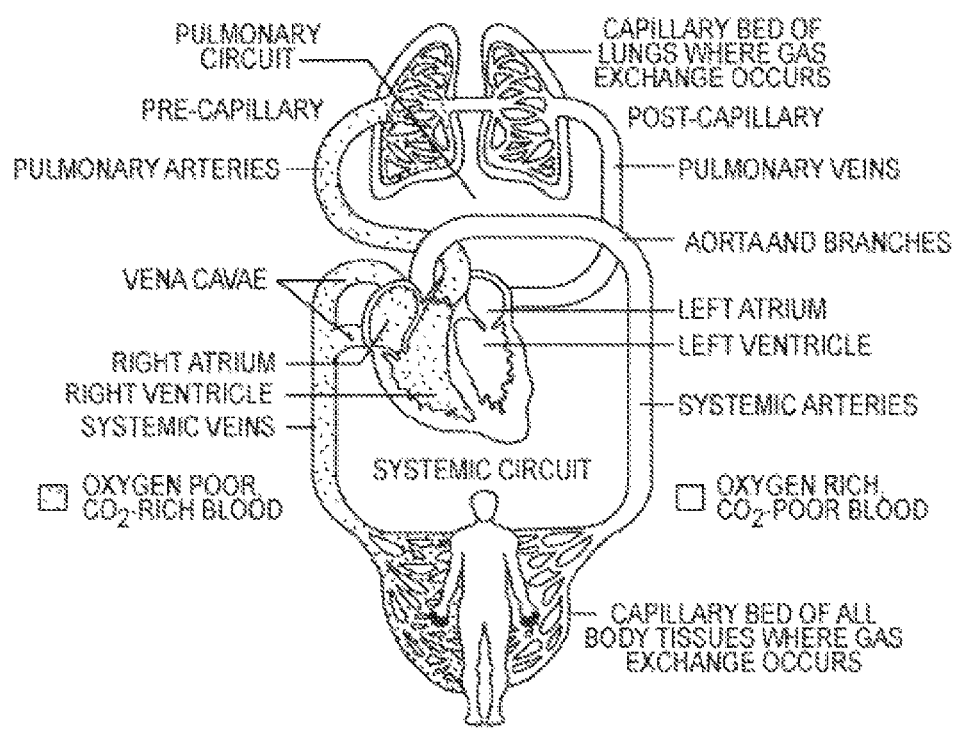
FIG. 1 shows a diagram of the circulatory system.

Provided herein are methods to provide lung-targeted therapies for patients with PAH, and other forms of PH, or other lung disorders, that is delivered to the pulmonary vascular bed with minimal systemic exposure via a dry powder inhaler. Such an appropriate inhaled medication would be characterized by good pulmonary tolerance and little or no systemic exposure and would lend itself to both targeted chronic maintenance therapy delivered 1, 2, 3, or more times per day and the potential for PRN (pro re nata; as circumstance dictates) use. All drugs used for chronic therapies have a peak and trough of efficacy in time and even long acting drugs with sustained benefit experience a decay in effect over time.

A PRN dosed medication for PH, if convenient to use, and portable, easily allows a patient to enhance their short-term function and exercise tolerance to accomplish day to day activities of daily living (ADL) or when wanting to perform other more vigorous activities. By avoiding the potential for ventilation/perfusion mismatching associated with systemic (enteral or parenteral) administration of pulmonary vasodilator drugs as well as the dose limiting systemic side effects, the provided methods of an inhaled pulmonary vasodilator delivered by a simple to use portable inhaler offers improved function and quality of life for patients with effort limitation due to PH and/or interstitial lung disease (ILD).

In some instances, self-administration of a lower dose of drug via inhalation, e.g., an inhaled PDE5i such as vardenafil, as a PRN therapy on top of chronic background therapies may provide patients with improved exercise tolerance throughout the day, while minimizing the risk of systemic side effects. Such PRN administration requires a drug product that is effectively targeted to the lungs and pulmonary blood vessels, while minimizing the drug concentration in the systemic circulation that contributes to drops in systemic blood pressure. Aerosol administration also provides a rapid onset of action (comparable to an injection) as compared to oral administration.

PRN administration via inhalation of vasodilators offers PH patients an opportunity to optimize their daily life function by self-administration of a lower nominal dose of drug, preparatory to increased activity to augment background therapy efficacy, would offer safe and effective improvement in quality of life indices and measures of daily function.

I. Definitions

The singular forms "a," "an," and, "the" include plural references unless the context clearly dictates otherwise. Thus, for example, reference to a compound refers to one or more compounds or at least one compound. As such, the terms "a" (or "an"), "one or more," and "at least one" can be used interchangeably herein.

The phrase "about" as used herein is used to provide flexibility to a numerical range endpoint by providing that a given value may be "a little above" or "a little below" the endpoint accounting for variations one might see in measurements taken among different instruments, samples, and sample preparations.

As used herein, the term "pulmonary hypertension" refers to increased blood pressure with the arteries of the lungs. Pulmonary arterial hypertension (PAH) is a chronic disease characterized by proliferation and remodeling of vascular endothelial and smooth muscle cells in the small pulmonary arteries and arterioles, resulting in a physical narrowing of the arteries, progressive increases in pulmonary vascular resistance, elevation in pulmonary artery pressure, right heart failure, and eventually, death.

As used herein, the term "interstitial lung disease," also termed pulmonary fibrosis, refers to diseases affecting the tissue and space around the air sacs of the lungs (e.g., alveolar epithelium, pulmonary capillary endothelium, basement membrane, perivascular and perilymphatic tissues). The term "idiopathic pulmonary fibrosis" refers to a condition characterized by progressive scarring of the lungs, usually occurring without a specified cause.

As used herein, the term "pulmonary artery" refers to an artery that carries deoxygenated blood from the right side of the heart to the lungs.

As used herein, the term "small airways" refers to small bronchi and bronchioles. The term "bronchi" refers to airways distal to the trachea, the walls of which contain cartilage, smooth muscle, and submucosal glands. Bronchi undergo multiple divisions along the bronchial tree, and the term "small bronchi" generally refers to bronchi between the lobar bronchi and the bronchioles. The term "bronchioles" refers to branches of the bronchi which do not contain cartilage or glands in the submucosa. In the context of the present disclosure, the small airways do not extend to the alveoli of the lungs.

The terms "therapeutic agent," "active agent," "active pharmaceutical ingredient," "API," "pharmaceutically active agent," and "pharmaceutical," and "drug" are used interchangeably herein to refer to a substance having a pharmaceutical, pharmacological, psychosomatic, or therapeutic effect. Further, when these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, solvates (such as hydrates), polymorphs, pseudopolymorphs, and esters.

As used herein, the term "log P" refers to octanol-water partition coefficient, which is a measure of hydrophobicity/hydrophilicity for a particular substance.

As used herein, the term "oral availability" refers to refers to the fraction of the total amount of an ingested micronutrient that ultimately reaches the systemic circulation. Thus, an oral bioavailability of 20% means that only 20% of the ingested amount of micronutrient reaches the systemic circulation.

As used herein, the term "systemic half-life" refers to the amount of time required for the level of a substance in the systemic circulation to be reduced by 50%.

As used herein, the term "vasodilator" refers to an active agent that causes enlargement of blood vessels. Examples of vasodilators include, but are not limited to, PDE5 inhibitors as described herein, soluble guanylate cyclase stimulators, nitroglycerin, and organic nitrites.

As used herein, the term "bronchodilator" refers to an active agent that causes expansion of bronchial air passages. The expansion can decrease resistance in the respiratory airway and increase airflow to the lungs. Examples of bronchodilators include, but are not limited to, $\beta_2$-agonists and anticholinergics.

As used herein, the terms "formulation" and "composition" are used interchangeably and refer to a mixture of at least one compound, element, or molecule. In some aspects the terms "formulation" and "composition" may be used to refer to a mixture of one or more active agents with one or more pharmaceutically acceptable excipients.

As used herein, the term "carrier-based composition" refers to an adhesive mixture comprising micronized drug particles with coarse carrier particles. Fine carrier particles, or a combination of coarse carrier particles and fine carrier particles, can also be included in the adhesive mixture.

As used herein, the term "engineered particles" refers to particles that have been engineered to achieve specific physicochemical properties that are advantageous for their intended use. In the context of inhalation, engineered particles are often prepared by bottom-up spray-drying processes which provide for control of particle size, density, rugosity, and surface composition, and consequent improvements in lung targeting and dose consistency.

As used herein, the term "portable inhaler" refers to an inhaler device (e.g., a dry powder inhaler or a metered-dose inhaler) that fits easily in a shirt pocket or purse, or is otherwise convenient to carry on one's person.

As used herein, the term "excipient" refers to any inert and pharmaceutically acceptable material that has substantially no biological activity, and makes up a substantial part of the composition so as to aid the administration of an active agent to a subject. By "pharmaceutically acceptable," it is meant that the excipient is compatible with the other ingredients of the composition and is not deleterious to the recipient thereof. Pharmaceutical excipients useful in the present invention include, but are not limited to, carriers, fillers, and force control agents.

As used herein, the term "force control agent" refers to an excipient utilized to control interparticle cohesive forces between particles. Force control agents are typically hydrophobic and include, but are not limited to, magnesium stearate, leucine, and long-chain saturated phospholipids (e.g., dipalmitoylphosphatidylcholine).

As used herein, the terms "nominal dose" and "ND" refer to the mass of drug that is administered in a single dose.

As used herein, the term "treating" refers to providing an appropriate dose of a therapeutic agent to a subject suffering from an ailment. An "acute" treatment (and/or an acute effect of such treatment) has an abrupt onset and short duration of action (e.g., less than 1 day), where as a "chronic" treatment lasts over a longer period of time (e.g., greater than three months).

As used herein, the term "daily treatment burden" refers to the time required to gather supplies, prepare delivery system, inhale drug product, and clean the delivery system on a daily basis. This is heavily influenced by the nature of the delivery system and the treatment regimen (i.e., how many times daily the drug is administered).

As used herein, the term "administration time" refers to the time required for inhalation therapy.

As used herein, the term "condition" refers to a disease state for which the compounds, compositions and methods of the present disclosure are being used to treat.

As used herein, "subject" refers to a mammal that may benefit from the administration of a drug composition or method of this invention. Examples of subjects include humans, and may also include other animals such as horses, pigs, cattle, dogs, cats, rabbits, rats, mice and aquatic mammals. In one specific aspect, a subject is a human.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, the terms "administration," and "administering" refer to the manner in which an active agent is presented to a subject. Administration can be accomplished by various art-known routes such as oral, parenteral, transdermal, inhalation, implantation, etc.

The term "pulmonary administration" represents any method of administration in which an active agent can be administered through the pulmonary route by inhaling an aerosolized liquid or powder form (nasally or orally). Such aerosolized liquid or powder forms are traditionally intended to substantially release and or deliver the active agent to the epithelium of the lungs. In certain embodiments, the active agent is in powder form.

The terms "nominal load" or "total load," also termed "fill mass," refer to the total amount of formulation packaged or partitioned for administration to a subject. For example, the nominal load is the total amount of powder composition that is enclosed in a capsule for use with an inhaler.

The term "nominal dose" or "total dose" refers to the total amount or mass of active agent packaged or partitioned for administration to a subject. For example, the nominal dose is the total amount of active agent that is enclosed in a capsule for use with an inhaler.

The term "emitted dose" (ED (%)) refers to the mass of an active agent that is emitted from a portable inhaler aerosolization device as a percentage of a nominal dose mass.

The term "fine particle fraction" (% FPF(ED)) refers to the mass of active agent having an aerodynamic diameter below 5 μm expressed as a percentage of the emitted dose. The FPF is often used to evaluate the efficiency of aerosol deagglomeration.

The aerodynamic diameter ($d_a$) is a spherical equivalent diameter and derives from the equivalence between the inhaled particle and a sphere of unit density ($\rho_0$) undergoing sedimentation at the same rate as per the following formula:

$$d_a = d_g \sqrt{\frac{\rho}{\chi \rho_0}} \quad \text{(Eq. 1)}$$

where $d_g$ is the volume-equivalent geometric diameter, $\rho$ is the particle density and $\chi$ is the dynamic shape factor. Hence, the aerodynamic behavior depends on particle geometry, density and volume diameter: a small spherical particle with a high density will behave aerodynamically as a bigger particle, being poorly transported in the lower airways. The $d_a$ can be improved reducing the volume diameter and the density or increasing the shape factor of the particles, by means of different processes.

The term "mass median aerodynamic diameter" (MMAD) refers to the mass median aerodynamic diameter of airborne particles at which 50% of particles by mass are larger and 50% are smaller. In other words, it is the median of the aerodynamic particle size distribution as a function of particle mass. The percentages of mass less than the stated aerodynamic diameters versus the aerodynamic diameters are plotted logarithmically. The MMAD is taken as the intersection of the line with the 50% cumulative percent for a log-normal distribution. Computational methods can also be applied.

The terms "volume weighted median diameter" and "Dv50" refer to the diameter for a population of particles, wherein half of the population resides above the specified value and half of the population resides below the specified value.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

II. Methods for Treating Pulmonary Hypertension

Provided herein are methods to provide lung-targeted therapies for patients with PAH, and other forms of PH, wherein a vasodilator is delivered to the pulmonary vascular bed with minimal off-target exposure via a portable inhaler. The inhaled medications provided herein are characterized by good pulmonary tolerance and little or no gastrointestinal or systemic exposure, making them particularly advantageous for PRN (pro re nata; as circumstance dictates) use. The methods and compositions disclosed herein benefit PH patients for whom chronic maintenance therapies are already prescribed because all drugs used for chronic maintenance therapies have a peak and trough of efficacy in time, and because even long acting drugs with sustained benefit experience a decay in effect over time.

A PRN dosed medication for PH, if convenient to use, and portable, easily allows a patient to enhance their short-term function, acutely improve their physical activity level, and exercise tolerance to enable them to accomplish day to day activities, including but not limited to activities of daily living (ADL), or when wanting to perform other more vigorous activities.

In some instances, self-administration of a lower dose of drug via inhalation (vs. oral dosing) as a PRN therapy on top of chronic background therapies may provide patients with improved exercise tolerance acutely at times throughout the day, while minimizing the risk of systemic side effects. The drug products provided herein are effectively targeted to the lungs and pulmonary blood vessels, while minimizing the drug concentration in the systemic circulation that contributes to drops in systemic blood pressure. Aerosol administration also provides a rapid onset of action (comparable to an intravenous injection), which is not generally provided by oral administration.

PRN administration of vasodilator drugs via inhalation offers PH patients an opportunity to optimize their daily life function by self-administration of a lower dose of drug (vs. oral or IV administration) in preparation for increased activity, so as to augment the efficacy of background therapy. As such, PRN therapeutics offer a means for safely and effectively improving a patient's quality of life indices and measures of daily activity and function.

For those patients with concomitant lung disease, aerosol administration of vasodilators also provides improvements in ventilation/perfusion mismatch that is often associated with systemic (enteral or parenteral) delivery or oral administration. This provides for the safe use of PRN vasodilators in WHO Group 3 PH patients with obstructive and/or interstitial lung disease. In addition, co-administration of a PRN vasodilator with a short-acting bronchodilator may reduce the impact of airway obstruction, leading to improvements in inspiratory capacity and cardiac output, while reducing dyspnea.

The methods described herein are useful for the treatment of lung conditions including pulmonary hypertension. The methods generally include administering to a subject in need thereof an effective amount of a vasodilator, wherein the vasodilator is administered to the subject via inhalation pro re nata (PRN) using a portable inhaler. Methods of treatment for pulmonary hypertension or other lung disorders as provided herein generally include delivery of a vasodilator (e.g., a phosphodiesterase-5 inhibitor (PDE5i) or another vasodilator) on a PRN basis via inhalation to a patient in need thereof. Also provided are low dose vasodilator formulations appropriate for such use. The vasodilator is formulated and the composition is selectively delivered to the lung at as low an efficacious dose as possible, minimizing systemic drug concentration, and with a minimal amount of drug delivered off target to the mouth and throat where it can be swallowed and enter the systemic circulation by the gastrointestinal system (off-target delivery). By targeting delivery more specifically to the lung and minimizing off target delivery, the overall dose delivered to the patient can be minimized, the local lung concentration of the drug can be maximized, and the concentration of the drug in the systemic circulation can be minimized.

Subjects treated with the compositions and methods disclosed herein have pulmonary hypertension or another lung disorder. For example, the subject may have pulmonary arterial hypertension, interstitial lung disease, or both. In some instances, the subject may have WHO Group 1 pulmonary arterial hypertension (PAH). For example, the subject may have idiopathic PAH (IPAH; WHO Group 1.1) or familial/heritable PAH (FPAH; WHO Group 1.2). In another example, the subject may have WHO Group 1.3 PAH induced by drugs or toxins. In another example, the subject may have WHO Group 1.4 PAH associated with disorders such as connective tissue diseases, human immunodeficiency virus (HIV) infection, portal hypertension, congenital heart disease (CHD), schistosomiasis, or Chronic hemolytic anemia. In another example, the subject may have WHO Group 1.6 (or WHO Group 1') PAH associated with pulmonary veno-occlusive disease (PVOD) or pulmonary capillary hemangiomatosis (PCH). In some instances, the subject may have Group 3 pulmonary hypertension due to lung diseases and/or hypoxemia, such as chronic obstructive pulmonary disease (COPD), interstitial lung disease (ILD) (including idiopathic pulmonary fibrosis (IPF)), other pulmonary diseases with mixed restrictive and obstructive pattern, and/or chronic exposure to high altitude. In another example, the subject may have WHO Group 4 chronic thromboembolic pulmonary hypertension (CTEPH). In another example, the subject may have WHO Group 5 pulmonary hypertension with unclear multifactorial mechanisms, such as hematological disorders (including myeloproliferative disorders and splenectomy), systemic disorders (including sarcoidosis, pulmonary Langerhans cell histiocytosis, lymphangioleiomyomatosis, neurofibromatosis, vasculitis), metabolic disorders (such as glycogen storage disease, Gaucher disease, thyroid disorders), and other conditions such as tumoral obstruction, fibrosing mediastinitis, chronic renal failure on dialysis.

A patient's quality of life improves as a function of the patient's ability and capacity to satisfy his or her needs. Described herein are drug/device combination products that are designed to be administered when the patient feels they need a "hemodynamic boost" in order to perform a specific activity (e.g., doing the laundry, playing with children, or going to the store or a concert). The products can improve patient quality of life via acute improvements in exercise tolerance, physical activity levels, and symptoms, when taken on top of existing background therapies. The PRN dosage forms disclosed herein are designed to align with unmet patient needs, including: a more convenient dosing schedule; a rapid onset of action; a suitable duration of action; a superior safety and tolerability profile relative to current maintenance therapies; and a non-invasive, portable, and convenient delivery system with a low daily treatment burden.

The products and methods provide for dose administration without a strict treatment regimen. Moreover, a medication designed to be used 'as-needed' can provide a significant boost for patients who adhere poorly to their chronic medication regimen, or for those patients who have a deficit in exercise tolerance at various times in the day as a result of their treatment regimen, even if fully adherent. In this regard, a PRN therapeutic can decrease or otherwise improve symptoms for patients who miss a dose, while allowing them to maintain their scheduled treatment regimen. The use of a PRN therapeutic can simplify medication counseling on skipped doses, e.g., if a dose is missed, a patient can be counseled to administer a dose of the PRN therapeutic and then resume the normal treatment schedule for their chronic medication.

Upon administration of the PRN dosage form, a patient will begin to feel relief of their symptoms quickly—in some cases, relief is felt essentially immediately. The PRN dosage forms provided herein have a rapid onset of action, with a maximum concentration of drug attained in the circulation in less than 15 min, e.g., less than 10 min or less than 5 min. Moreover, the pharmacodynamic effects (e.g., improved hemodynamics, gas exchange, and symptom improvement) occur in under 30 min, with measurable improvements within 15 min or 10 min or less post-administration. Administration of vasodilators via inhalation, as described herein, provide a rapid onset of action with $t_{max}$ values for vasodilators well below one hour. For example, inhaled vardenafil has a $t_{max}$ of 2 min or less following pulmonary administration. In contrast, $t_{max}$ values for commonly oral vasodilators typically range from 2-8 hours. While intravenous injectables provide for immediate drug levels in the circulation, they are less suitable as PRN therapeutics, because dose delivery is highly invasive, provides high systemic drug levels leading to significant adverse events, and the treatment is inconvenient to administer by the patient on an as-needed basis without the use of complex pump systems.

Importantly, the PRN therapeutics disclosed herein provide symptom relief and improvements in exercise tolerance over a duration long enough to complete a target activity. In general, the duration of action is at least 1 h, extending to more than 2 h, to more than 3 h, or to longer extended periods.

The PRN therapeutics disclosed herein maximize the amount of drug delivered to the pulmonary arteries, while minimizing off-target delivery of the drug (e.g., gastrointestinal delivery and systemic delivery), so as to minimize safety and tolerability issues. Targeted delivery to the lungs is maximized by administration of aerosols via oral inhalation. A superior adverse event profile is a particular important advantage of a PRN therapeutic, given that the drug is administered on top of background therapies. Injectables lead to high systemic drug levels and to significant adverse events making them less suitable for PRN administration.

A. Active Agents

The therapeutic target for the vasodilators disclosed herein are the smooth muscle cells within the pulmonary arteries and arterioles. A key goal for a PRN therapeutic is to maximize drug delivered to the pulmonary arteries while minimizing off-target delivery of the drug to the mouth and throat where it is swallowed, so as to minimize safety and tolerability issues. For inhaled therapeutics, improvements in lung targeting is achieved not only by more effective drug delivery to the lungs, but also by rational design and/or selection of the drug to be delivered.

The key goals for a PRN therapeutic focused on pulmonary targeting are diametrically opposed to an oral therapeutic. For an orally administered therapeutic the goal is to maximize and maintain concentrations of drug in the systemic circulation. This is achieved by maximizing oral bioavailability, and then maintaining systemic concentrations of 'free' drug by minimizing protein binding and systemic clearance. In contrast, the pulmonary PRN therapeutic seeks to maximize the residence time in the lungs, either by having prolonged binding times to receptors, by slowing dissolution of drug in epithelial lining fluid, or by developing controlled release dosage forms (e.g., liposomes). Once absorbed into the systemic circulation, the goal is to minimize systemic effects, by having the drug cleared as rapidly as possible and/or be bound to plasma proteins. Moreover, minimizing oral bioavailability is also important to minimize systemic levels of drug arising from drug that is deposited in the upper respiratory tract following inhalation.

In preferred embodiments, the vasodilator is lipophilic with an octanol-water partition coefficient greater than zero (i.e., log P>0) to facilitate rapid absorption across cellular membranes. In some embodiments, the vasodilator exhibits an oral bioavailability less than 20%. In some embodiments, the vasodilator exhibits protein binding in the systemic circuit greater than 90%. In some embodiments, the vasodilator exhibits a half-life in the systemic circuit of under 6 h. In some embodiments, the vasodilator exhibits a half-life on the target receptor in the pulmonary arteries of greater than 30 min.

As described above, oral delivery is disadvantageous for PRN vasodilator therapy, due to the slow absorption times associated with oral administration, with the time to peak concentrations in the systemic circulation generally greater than 1 hr, and often much longer. The slow absorption times for oral therapeutics is due in large part to extensive first pass effects. In contrast, small molecule drugs are generally rapidly absorbed into the systemic circulation following pulmonary administration. Lipophilic drugs (log P>0) are particularly advantageous for absorption via the transcellular route, with absorption times around 1 min, whereas hydrophilic drugs with an octanol-water partition coefficient less than zero (i.e., log P<0) are typically absorbed through the lungs via the paracellular route with an absorption time of about 1 h. For example, inhaled vardenafil (log P=1.4) has a $t_{max}$ of 2 min or less (peak at first time-point tested) following pulmonary administration. Thus, in certain embodiments, vardenafil and other preferred vasodilators (sildenafil, log P=1.9; tadalafil, log P=1.7; avanafil, log P=2.6; epoprostenol, log P=2.9; iloprost, log P=4.8; treprostinil, log P=4.1; bosentan, log P=3.7) may rapidly cross the epithelial membrane in the lungs and the vascular endothelium into pulmonary arteries.

Residence time in the lungs can be maximized by selecting active agents having prolonged binding times to receptors. For PDE5 inhibitors, sildenafil has a half-life at the catalytic site on the PDE enzyme of just 3 min, and tadalafil 7 min. In contrast, vardenafil has a half-life of about 2 hr. Given the desire for acute improvements in exercise tolerance and symptoms of a PRN therapy over a period of hours, the 2 hr half-life of vardenafil on the receptor is particularly advantageous. The strong binding of vardenafil to the receptor ensures that efficacy will be maintained over the desired duration, even when systemic concentrations of vardenafil are at sub-therapeutic levels.

Most of the other currently marketed vasodilators for the treatment of PH (e.g., prostacyclins, PDE5i) have short binding times to receptors, thus requiring that systemic drug levels be maintained at a therapeutic level over the desired duration of action. The higher drug levels required in the systemic circulation under this circumstance, enhances the potential for adverse events. In a preferred embodiment, the vasodilator is vardenafil, which has a prolonged binding time to the catalytic binding site on the PDE5 enzyme.

Once absorbed into the systemic circulation, systemic effects can be minimized by ensuring that the drug is cleared as rapidly as possible and/or be bound to plasma proteins. For an inhaled therapeutic, drug that is deposited in the upper respiratory tract will be swallowed, and ultimately absorbed into the systemic circulation which can lead to off-target effects. As such, systemic drug levels can be minimized by selecting active agents with low (minimal) oral bioavailability. Off-target effects can also be minimized by selecting active agents to which plasma proteins (e.g., human serum albumin, α-globulins, β-globulins, immunoglobulins) bind strongly. These considerations stand in marked contrast to therapeutic agent delivered via oral administration. For an orally administered therapeutic, the goal is to maximize and maintain concentrations of drug in the systemic circulation. This is achieved by maximizing oral bioavailability, and then maintaining systemic concentrations of "free" drug by minimizing protein binding and the rate of clearance. All of the various classes of vasodilators exhibit extensive protein binding in the systemic circuit: sildenafil (96%), tadalafil (94%), vardenafil (93-95%), avanafil (99%), selexipag (>99%), bosentan (98%), and macitentan (>99%), making them all advantageous in this regard for use as PRN therapeutics. Many of the vasodilators also have low oral bioavailability, such as vardenafil (15%) and treprostinil (18%), making them particularly suitable in this regard for use as PRN therapeutics.

In certain instances, the PRN use of a vasodilator such as an inhaled PDE5 inhibitor is advantageous when the patient is also taking multiple oral drugs, or oral and IV- or subcutaneously-delivered drugs, at the same time in combination therapy for treating PH. The lower systemic blood level resulting from an inhaled vasodilator adds little to the side effect profile, increasing the dosing safety of the therapy as compared to an oral vasodilator when taken in addition to the combination therapy regimen, while minimizing the risk of hypoxia.

In a related embodiment, methods are provided which further comprise administering an effective amount of a second drug to the subject. In some instances, the second drug may be a vasodilator with a different mechanism of action. Such drugs may have complimentary or synergistic beneficial effects locally when delivered in combination via inhalation for the treatment of pulmonary hypertension. When the first drug is a PDE5 inhibitor, for example, the second drug may comprise at least one soluble guanylate cyclase stimulator, prostacyclin, prostacyclin analog, a prostacyclin receptor agonist or a combination thereof.

These drugs may be administered as combinations, for example, where each drug is formulated and administered separately or, alternatively, the drugs may be co-formulated in a fixed dose combination. Currently, co-administration of PDE5i and sGCS are contraindicated due to concerns regarding systemic hypotension. In certain embodiments, the improved selectivity for a PRN PDE5i may permit these drugs to be co-administered.

It may also be advantageous to administer fixed dose combinations of inhaled vasodilators with inhaled bronchodilators (either $\beta_2$-agonists or anticholinergics). These formulations are expected to have synergistic benefits in reducing dyspnea and improving symptoms in PH patients. Particularly preferred bronchodilators are those that have a pharmacokinetic and pharmacodynamic properties that match the vasodilator that they are to be paired with. Particularly preferred are short-acting bronchodilators such as albuterol and ipratropium.

1. PDE5 Inhibitors

Phosphodiesterase type 5 inhibitors (PDE5i) inhibit phosphodiesterase type 5 (PDE5) enzyme, which is responsible for the degradation of cyclic guanosine monophosphate (cGMP). Pulmonary arterial hypertension is associated with impaired release of nitric oxide (NO) by the vascular endothelium and consequent reduction of cGMP concentrations in the pulmonary vascular smooth muscle. PDE5 is the predominant phosphodiesterase in the pulmonary vasculature. Inhibition of PDE5 by PDE5 inhibitors increases the concentrations of cGMP, resulting in relaxation of pulmonary vascular smooth muscle cells and vasodilation of the pulmonary vascular bed. The PDE5i class of drugs appropriate for use in the invention includes sildenafil, tadalafil, vardenafil, avanafil, benzamidenafil, lodenafil, mirodenafil, udenafil, zaprinast, and others. Sildenafil and tadalafil are approved by the U.S. Food & Drug Administration for use in treating PAH.

In some embodiments, the PDE5i drug is selected from a pyrazolopyrimidinone, a pyriazino(pyrido)indole, an azapurinone, an amino(benzylamino)pyrimidine carboxamide, and an imidazotriazinone. Sildenafil (i.e., 1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine and salts thereof, such as a citrate salt) and other pyrazolopyrimidinones are described, for example, in U.S. Pat. Nos. 5,250,534; 5,346,901; and 5,719,283 which are incorporated herein by reference in their entirety. Tadalafil (i.e., (6R,12aR)-2,3,6,7,12,12a-hexahydro-2-methyl-6-(1,3-benzodioxol-5-yl)-pyrazino[1',2':1,6]pyrido[3,4-b]indole-1,4-dione, or a salt thereof) and other pyrazino(pyrido)indoles are described, for example, in U.S. Pat. Nos. 5,859,006; 6,140,329; 6,821,975; 6,943,166; and 7,182,958, which are incorporated herein by reference in their entirety. Zaprinast (i.e., 5-(2-propoxyphenyl)-1H-[1,2,3]triazolo[4,5-d]pyrimidin-7(4H)-one or a salt thereof) and other azapurinones are described, for example, in U.S. Pat. Nos. 3,987,160 and 4,039,544, which are incorporated herein by reference in their entirety. Avanafil, (i.e., (S)-4-[(3-chloro-4-methoxybenzyl)amino]-2-[2-(hydroxymethyl)-1-pyrrolidinyl]-N-(2-pyrimidinylmethyl)-5-pyrimidinecarboxamide or a salt thereof) and other amino(benzylamino)pyrimidine carboxamides are described, for example, in U.S. Pat. Nos. 6,656,935 and 7,501,409, which are incorporated herein by reference in their entirety. In some embodiments, the PDE5i drug is selected from sildenafil, tadalafil, zaprinast, avanafil, and vardenafil.

In a preferred embodiment, the PDE5i drug is vardenafil (i.e., 1-[[3-(1,4-dihydro-5-methyl-4-oxo-7-propylimidazo[5,1-f][1,2,4]triazin-2-yl)-4-ethoxyphenyl]sulfonyl]-4-ethyl-piperazine, or a pharmaceutically acceptable salt thereof, such as a monohydrochloride salt). Vardenafil and other 2-phenyl substituted imidazotriazinones are described, for example, in U.S. Pat. Nos. 6,890,922; 7,122,540; 7,314,871; 7,704,999; and 7,696,206, which are incorporated herein by reference in their entirety. Vardenafil has been shown to be safe and effective in human patients with PAH at a dose of 5 mg, administered orally twice per day (b.i.d.) (Jing, 2009; Jing 2011). Vardenafil has been shown to have characteristics superior to sildenafil and tadalafil for use as an inhaled agent and has been formulated into a dry powder and delivered by a dry powder inhaler device as described in International PCT Appl. No. WO/2015/089105 and U.S. Patent Appl. No. 2016/0317542, which are incorporated by reference herein in their entireties. Vardenafil has been reported to be inhaled and well tolerated by normal patients in an erectile dysfunction study (Berry, 2009; Berry, 2016).

2. sGC Stimulators

In some embodiments, the vasodilator may be a sGC stimulator. The sGC stimulator can be a heteroaryl-fused pyrazole such as riociguat (i.e., methyl 4,6-diamino-2-[1-(2-fluorobenzyl)-1H-pyrazolo[3,4-b]pyridin-3-yl]-5-pyrimidinyl(methyl)carbamate or a salt thereof). Riociguat and other heteroaryl-fused pyrazoles are described, for example, in U.S. Pat. Nos. 6,743,798 and 7,173,037.

Guanylate cyclase stimulators (sGCs) act on soluble guanylate cyclase (sGC), an enzyme in the cardiopulmonary system and the receptor for nitric oxide (NO). When NO binds to sGC, the enzyme catalyzes synthesis of the signaling molecule cyclic guanosine monophosphate (cGMP). Intracellular cGMP plays an important role in regulating processes that influence vascular tone, proliferation, fibrosis, and inflammation. Pulmonary hypertension is associated with endothelial dysfunction, impaired synthesis of nitric oxide, and insufficient stimulation of the NO-sGC-cGMP pathway. An exemplary sGCS is riociguat. Riociguat has a dual mode of action: it sensitizes sGC to endogenous NO by stabilizing the NO-sGC binding and also directly stimulates sGC via a different binding site, independently of NO. Riociguat stimulates the NO-sGC-cGMP pathway and leads to increased generation of cGMP with subsequent vasodilation.

The efficacy of sGC drugs is related to the generation of cyclic GMP. GMP is broken down in the lung by phosphodiesterases (of which the most common in the lung is phosphodiesterase-5; PDE5). Inhibition of PDE5 potentiates the action of cyclic GMP, which is the mechanism of action for all the oral PDE5i drugs approved for the treatment of PAH (such as tadalafil and sildenafil). However, the systemic effect of these drugs when taken concomitantly results in significant symptomatic hypotension. In the described method, the effect of the PDE5i and, hence, the potentiation of the cyclic GMP, is restricted to the pulmonary vascular bed by selectively dosing lungs via an inhaled delivery route, and the vasodilator effect may be potentiated. This treatment would benefit both PAH and CTEPH patients. Importantly, although riociguat activates soluble guanylate cyclase in both an NO-dependent and NO-independent fashion, its action should be potentiated by inhibition of phosphodiesterase 5. Oral sGC and oral PDE5i are contraindicated to be taken concomitantly at recommended oral doses because of the risk of systemic hypotension. In some instances, the drugs are delivered concomitantly or sequentially via inhalation at doses of $1/10^{th}$ to $1/20^{th}$ or lower of the oral dose concentration of either drug, thereby resulting in a synergistic effect, making more cGMP available (via sGCS increasing cyclic GMP) and by the PDE5i preventing the degradation of cGMP (via PDE5i). As a result, subsequent vascular smooth muscle relaxation in the pulmonary vasculature may take place at lower concentrations of either drug taken as a mono therapy. Similar synergistic activity is contemplated with other drug combinations as well. In general, much lower doses of both drugs are required when the drugs are inhaled vs. taken via the oral or IV or subcutaneous delivery routes.

3. Prostacyclin and Prostacyclin Analogs

In another example, the vasodilator may be prostacyclin, a naturally-occurring prostaglandin also referred to as epoprostenol (i.e., (5Z,9α,11α,13E,15S)-6,9-epoxy-11,15-dihydroxyprosta-5,13-dien-1-oic acid). Epoprostenol and related compounds are described, for example, in U.S. Pat. Nos. 4,883,810; 4,883,812; 8,318,802; and 8,598,227, which are incorporated herein by reference in their entirety.

In another example, the vasodilator may be a prostacyclin analog. The prostacyclin analog can be a benzindene prostaglandin such as treprostinil (i.e., (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid or a salt thereof). Tresprostinil and other benzindene prostaglandins are described, for example, in U.S. Pat. Nos. 4,306,075; 6,521,212; 6,756,033; 6,765,117; 8,497,393; 9,339,507; 9,358,240; 9,593,066; and 9,604,901, which are incorporated herein by reference in their entirety.

The prostacyclin analog can be an acetylenic prostacyclin analog containing an alkyne moiety, such as iloprost (i.e., (E)-(3aS, 4R, 5R, 6aS)-hexahydro-5-hydroxy-4-[(E)-(3S, 4RS)-3-hydroxy-4-methyl-1-octen-6-ynyl]-$\Delta^{2(1H),\Delta}$-pentalenevaleric acid or a salt thereof, such as a sodium salt) or beraprost (i.e., 2,3,3a,8b-tetrahydro-2-hydroxy-1-(3-hydroxy-4-methyl-1-octen-6-yn-1-yl)-1H-cyclopenta[b]benzofuran-5-butanoic acid, or a salt thereof). Iloprost, beraprost, and other acetylenic prostacyclin analogs are described, for example, in U.S. Pat. Nos. 4,474,802; 5,124,267.

4. Prostacyclin Receptor Agonists

In another example, the vasodilator may be a prostacyclin receptor agonist. The prostacyclin receptor agonist can be a diphenylpyrazine such as selexipag (i.e., 2-{4-[(5,6-diphenylpyrazin-2-yl)(isopropyl)amino]butoxy}-N-(methylsulfonyl) acetamido) or a salt thereof. Selexipag and other diphenylpyrazines are described, for example, in U.S. Pat. Nos. 7,205,302; 8,791,122; 9,173,881; and 9,284,280, which are incorporated herein by reference in their entirety. The prostacyclin receptor agonist can be a pyridopyrazine such as QCC374 (i.e., 7,8-dihydro-2,3-bis(4-methylphenyl)-pyrido[2,3-b]pyrazine-5(6H)-heptanoic acid, or a salt thereof). QCC374 and other pyridopyrazines are describe, for example, in U.S. Pat. Nos. 8,754,085 and 9,132,127, which are incorporated herein by reference in their entirety. The prostacyclin receptor agonist can be a cyclohexane derivative such as ralinepag (i.e., 2-[[trans-4-[[[[(4-chlorophenyl)phenylamino]carbonyl]oxy]methyl]-cyclohexyl] methoxy] acetic acid or a salt thereof). Ralenipag and other cyclohexane derivatives are described, for example, in U.S. Pat. No. 8,895,776 and WO 2011/037613, which are incorporated herein by reference in their entirety.

5. Bronchodilators

Bronchodilators such as beta-agonists and anticholinergics can also be used in the compositions and methods provided herein. In some embodiments, the methods for treating pulmonary hypertension include administering a vasodilator and one or more bronchodilators selected from the group consisting of a short-acting beta-agonist, a long-acting beta agonist, a short-acting anticholinergic, and a long-acting anticholinergic. Examples of short-acting beta-agonists include, but are not limited to, albuterol, levalbuterol, pirbuterol, terbutaline, and metaproteranol. Long-acting beta-agonists include, but are not limited to, formoterol, salmeterol, vilanterol, indacaterol, bambuterol, clenbuterol, and oladaterol. Short-acting anticholinergics include, but are not limited to, ipratropium. Long-acting anticholinergics include, but are not limited to, tiotropium, glycopyrrolate, aclidinium, and umeclidinium.

B. Dosing

In the provided methods, when a patient is anticipating physical exertion such as, for example, exercising, taking a walk, a trip to the store, or other activity, the subject administers via inhalation the PRN formulation, comprising a vasodilator (e.g., a PDE5i drug) alone or combination with a second drug (either co-formulated or packaged separately). Typically, the patient administers the formulation(s) 2-30 minutes before initiating such activity. The patient administers these doses in addition to any chronic therapies they are taking. The dose of the vasodilator, or the combination of drugs as described above, would be sufficiently low as to not cause significant additive side effects to the baseline drug regimen the patient is taking, but would be sufficient to transiently dilate pulmonary blood vessels for at least 30 minutes up to at least 6 hours, allowing patients to enhance their exercise tolerance and complete their desired ADLs.

In some embodiments, the PRN therapeutic comprises one or more active agents selected from the group consisting of a PDE5 inhibitor, an sGC stimulator, prostacyclin, a prostacyclin analog, and a prostacyclin receptor analog (including any of the specific substances set forth above) in a nominal dose ranging from 0.1 to 5.0 mg (e.g., from 0.15 to 0.5 mg). In some embodiments, the PRN therapeutic comprises one or more active agents selected from the group consisting of a PDE5 inhibitor, an sGC stimulator, prostacyclin, a prostacyclin analog, and a prostacyclin receptor analog (including any of the specific substances set forth above) in a nominal dose ranging from 0.02 to 1.0 mg (e.g., from 0.04 to 0.1 mg). As a non-limiting example, the nominal dose of vardenafil (in base form) for an inhaled PRN therapeutic formulated in a carrier-based formulation and delivered with a capsule-based dry powder inhaler typically ranges from about 0.1 mg to about 2.0 mg, (e.g., between 0.15 and 0.50 mg). The fill mass is typically between 12.5 mg and 25 mg. The emitted dose for a carrier-based composition of vardenafil with a capsule-based dry powder inhaler is typically greater than 70% of the nominal dose (e.g., greater than 80% of the nominal dose). As a non-limiting example, the nominal dose of treprostinil or OCC374 for an inhaled PRN therapeutic formulated in a carrier-based formulation and delivered with a capsule-based dry powder inhaler typically ranges from about 0.02 mg to about 1.0 mg, (e.g., between 0.04 and 0.10 mg).

In another aspect of this disclosure, the total lung dose (TLD) of the drug composition comprising micronized drug and carrier is greater than 20% of the delivered dose, e.g., greater than 35% of the delivered dose, greater than 40% of the delivered dose, greater than 50% of the delivered dose, greater than 60% of the delivered dose, or higher. In some instances, the TLD of the composition is at least 25%, 30%, 35%, 40%, 45%, 50%, 55%, 60%, 65%, 70%, 75%, 80%, 85%, 90%, 95%, or 99% of the delivered dose. In some instances, the TLD of the composition is at least 25%, 30%, 35%, 40%, 45%, 50%, 55%, or 60% of the delivered dose. The total lung dose may be determined using the Alberta Idealized Throat (AIT) model at a pressure drop across the inhaler device of 4 kPa. The AIT model has been demonstrated to provide excellent in vitro to in vivo correlations in terms of TLD. See, e.g., DeHaan, 2004; Finlay, 2010; Olsson, 2013; Delvadia, 2013; Weers 2015. Currently marketed lactose blend compositions (without force control agents) have a TLD between 5% and 40%, depending on the nature of the drug and the delivery device. Improvements in TLD, which correlate to improvements in lung targeting, provide reductions in dose and minimize gastrointestinal absorption contributions to systemic delivery.

In some embodiments, a carrier-based composition of vardenafil that is administered with a portable dry powder inhaler is provided, wherein the total lung dose (TLD) is greater than 35% (w/w) of the emitted dose (e.g., greater than 40% (w/w) of the emitted dose or greater than 50% (w/w) of the emitted dose).

In some embodiments, a carrier-based composition of vardenafil containing an added force agent that is administered with a portable dry powder inhaler is provided, wherein the total lung dose (TLD) is greater than 40% (w/w) of the emitted dose (e.g., greater than 50% w/w of the emitted dose).

As another non-limiting example, a low-density engineered particle formulation of vardenafil may have a fill mass ranging from about 1 mg to about 10 mg (e.g., 3 mg), an emitted dose ranging from about 80% to about 95% (e.g., greater than 90%). The TLD for a low-density engineered particle formulation can be two-fold higher (or greater) than a carrier-based formulation, leading to nominal doses two-fold lower (or less) than a carrier-based formulation with the same capsule-based inhaler.

As another non-limiting example, the nominal dose of treprostinil for an inhaled PRN therapeutic formulated as a solution-based formulation and delivered with a portable smart-mist inhaler typically ranges from about 10 µg to about 100 µg, (e.g., between 20 and 50 µg). The metering volume within the smart-mist inhaler is ca., 10 to 20 µL, with a dissolved treprostinil concentration of up to 10 mg/ml.

In some instances, a dose of $\frac{1}{10}^{th}$ to $\frac{1}{50}^{th}$ or less of an oral dose typically used for oral vasodilators (e.g., oral PDE5i drugs) or other drugs may be used for each drug in such combination formulations and methods of treatment. Low doses such as these may be as or more effective when delivered via the lung and result in fewer side effects, especially if their mechanisms of action are synergistic. Such doses are desired whether the drugs are co-formulated as mixture or formulated and packaged separately.

In some instances, the inhaled dose required to attain efficacy in a human subject with pulmonary hypertension or other lung disease as described herein may be about $\frac{1}{10}^{th}$ to $\frac{1}{50}^{th}$ the oral dose. Formulations may be packaged having a fill mass of 5-20 mg or higher of the formulation. Formulations of various different doses are contemplated, including, for example, formulations having inhaled dosages from 0.01 mg to 5 mg of active agent of PDE5i delivered to the lung. In some instances, where the second drug is a sGCS drug, the formulation may have a sGCS inhaled dose of 0.001 mg to 0.5 mg of active sGCS drug delivered to the lung.

For example, the PDE5i inhaled dose may be in the range of 0.01 mg to 0.5 mg, 0.01 mg to 1 mg, 0.01 mg to 2 mg, 0.025 mg to 0.5 mg, 0.025 mg to 1 mg, 0.025 mg to 2 mg, 0.05 mg to 0.5 mg, 0.05 mg to 1 mg, 0.05 mg to 2 mg, 0.075 mg to 0.5 mg, 0.075 mg to 1 mg, 0.075 mg to 2 mg, 0.1 mg to 0.25 mg, 0.1 mg to 0.5 mg, 0.1 mg to 1 mg, 0.1 mg to 2 mg, 0.1 mg to 3 mg, 0.1 mg to 4 mg, 0.25 mg to 0.5 mg, 0.25 mg to 0.75 mg, 0.25 mg to 1 mg, 0.25 mg to 1.5 mg, 0.25 mg to 2 mg, 0.25 mg to 3 mg, 0.25 mg to 4 mg, 0.5 mg to 0.75 mg, 0.5 mg to 1 mg, 0.5 mg to 2 mg, 0.5 mg to 1 mg, 0.5 mg to 2 mg, 0.5 mg to 3 mg, 0.5 mg to 4 mg, 0.75 mg to 1 mg, 0.75 mg to 2 mg, 0.75 mg to 1 mg, 0.75 mg to 2 mg, 0.75 mg to 3 mg, 0.75 mg to 4 mg, 1 mg to 1.5 mg, 1 mg to 2 mg, 1 mg to 2.5 mg, 1 mg to 3 mg, 1 mg to 3.5 mg, 1 mg to 4 mg, 2 mg to 3 mg, 2 mg to 4 mg, 0.5 mg to 4.5 mg, 2 mg to 5 mg, and doses within 25% of these ranges. In some such embodiments, the PDE5i drug is vardenafil.

In some instances, the PDE5i composition may have an inhaled dose of 0.01 mg, 0.25 mg, 0.05 mg, 0.075 mg, 0.1 mg, 0.125 mg, 0.15 mg, 0.175 mg, 0.2 mg, 0.225 mg, 0.25 mg, 0.275 mg, 0.3 mg, 0.325 mg, 0.35 mg, 0.375 mg, 0.4 mg, 0.425 mg, 0.45 mg, 0.5 mg, 0.525 mg, 0.55 mg, 0.575 mg, 0.6 mg, 0.625 mg, 0.65 mg, 0.675 mg, 0.7 mg, 0.725 mg, 0.75 mg, 0.775 mg, 0.8 mg, 0.825 mg, 0.85 mg, 0.875 mg, 0.9 mg, 0.925 mg, 0.95 mg, 0.975 mg, 1.0 mg, 1.1 mg, 1.15 mg, 1.2 mg, 1.25 mg, 1.3 mg, 1.35 mg, 1.4 mg, 1.45 mg, 1.5 mg, 1.55 mg, 1.6 mg, 1.65 mg, 1.7 mg, 1.75 mg, 1.8 mg, 1.85 mg, 1.9 mg, 1.95 mg, 2.0 mg, 2.1 mg, 2.15 mg, 2.2 mg, 2.25 mg, 2.3 mg, 2.35 mg, 2.4 mg, 2.45 mg, 2.5 mg, 2.55 mg, 2.6 mg, 2.65 mg, 2.7 mg, 2.75 mg, 2.8 mg, 2.85 mg, 2.9 mg, 2.95 mg, 3.0 mg, 3.1 mg, 3.15 mg, 3.2 mg, 3.25 mg, 3.3 mg, 3.35 mg, 3.4 mg, 3.45 mg, 3.5 mg, 3.55 mg, 3.6 mg, 3.65 mg, 3.7 mg, 3.75 mg, 3.8 mg, 3.85 mg, 3.9 mg, 3.95 mg, 4.0 mg, 4.1 mg, 4.15 mg, 4.2 mg, 4.25 mg, 4.3 mg, 4.35 mg, 4.4 mg, 4.45 mg, 4.5 mg, 4.55 mg, 4.6 mg, 4.65 mg, 4.7 mg, 4.75 mg, 4.8 mg, 4.85 mg, 4.9 mg, 4.95 mg, 5.0 mg, or a dose within 25% of any of these doses. In some such embodiments, the PDE5i drug is vardenafil.

In some instances, the PDE5i composition may have an inhaled dose of at least about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.4 mg, 3.5 mg, 3.6 mg. 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, or 5 mg. In some instances, the PDE5i composition may have an inhaled dose of no more than about 0.1 mg, no more than about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.4 mg, 3.5 mg, 3.6 mg. 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, or 5 mg. In some instances, the subject may receive a daily inhaled dose of the PDE5i composition of 0.25 mg to 1 mg, 0.1 mg to 4 mg, 0.1 mg to 2 mg, 1 mg to 4 mg, or a dose within 25% of these ranges. In some such embodiments, the PDE5i drug is vardenafil.

In some instances, the PDE5i composition may have an inhaled dose of at least about 0.001 mg, 0.0025 mg, 0.005 mg, 0.0075 mg, 0.01 mg, 0.0125 mg, 0.015 mg, 0.0175 mg, 0.02 mg, 0.025 mg, 0.0275 mg, 0.03 mg, 0.0325 mg, 0.035 mg, 0.0375 mg, 0.04 mg, 0.0425 mg, 0.05 mg, 0.0525 mg, 0.055 mg, 0.0575 mg, 0.06 mg, 0.0625 mg, 0.065 mg, 0.0675 mg, 0.07 mg, 0.0725 mg, 0.075 mg, 0.0775 mg, 0.08 mg, 0.0825 mg, 0.085 mg, 0.0875 mg, 0.09 mg, 0.0925 mg, 0.095 mg, 0.0975 mg, 0.1 mg, 0.125 mg, 0.15 mg, 0.175 mg, 0.2 mg, 0.225 mg, 0.25 mg, 0.275 mg, 0.3 mg, 0.325 mg, 0.35 mg, 0.375 mg, 0.4 mg, 0.425 mg, 0.45 mg, 0.475 mg, 0.5, or a dose within 25% of any of these doses. In some such embodiments, the PDE5i drug is vardenafil.

In some instances, the PDE5i composition may have an inhaled dose of no more than about 0.001 mg, 0.0025 mg, 0.005 mg, 0.0075 mg, 0.01 mg, 0.0125 mg, 0.015 mg, 0.0175 mg, 0.02 mg, 0.025 mg, 0.0275 mg, 0.03 mg, 0.0325 mg, 0.035 mg, 0.0375 mg, 0.04 mg, 0.0425 mg, 0.05 mg, 0.0525 mg, 0.055 mg, 0.0575 mg, 0.06 mg, 0.0625 mg, 0.065 mg, 0.0675 mg, 0.07 mg, 0.0725 mg, 0.075 mg, 0.0775 mg, 0.08 mg, 0.0825 mg, 0.085 mg, 0.0875 mg, 0.09 mg, 0.0925 mg, 0.095 mg, 0.0975 mg, 0.1 mg, 0.125 mg, 0.15 mg, 0.175 mg, 0.2 mg, 0.225 mg, 0.25 mg, 0.275 mg, 0.3 mg, 0.325 mg, 0.35 mg, 0.375 mg, 0.4 mg, 0.425 mg, 0.45 mg, 0.475 mg, 0.5, or a dose within 25% of any of these doses. In some instances, the subject may receive a daily inhaled dose of 0.003 mg to 1 mg, 0.015 mg to 0.75 mg, 0.075 mg to 0.375 mg, 0.075 mg to 0.75 mg, or a dose within 25% of these ranges. In some such embodiments, the PDE5i drug is vardenafil.

For example, the sGCS drug inhaled dose may be in the range of 0.001 mg to 0.5 mg, 0.001 mg to 0.05 mg, 0.001 mg to 0.025 mg, 0.001 mg to 0.05 mg, 0.001 mg to 0.075 mg, 0.001 mg to 0.1 mg, 0.001 mg to 0.15 mg, 0.001 mg to 0.2 mg, 0.001 mg to 0.25 mg, 0.001 mg to 0.3 mg, 0.001 mg to 0.35 mg, 0.001 mg to 0.4 mg, 0.001 mg to 0.5 mg, 0.01 mg to 0.05 mg, 0.01 mg to 0.025 mg, 0.01 mg to 0.05 mg, 0.01 mg to 0.075 mg, 0.01 mg to 0.1 mg, 0.01 mg to 0.15 mg, 0.01 mg to 0.2 mg, 0.01 mg to 0.25 mg, 0.01 mg to 0.3 mg, 0.01 mg to 0.35 mg, 0.01 mg to 0.4 mg, 0.01 mg to 0.5 mg, 0.025 mg to 0.05 mg, 0.025 mg to 0.075 mg, 0.025 mg to 0.1 mg, 0.025 mg to 0.15 mg, 0.025 mg to 0.2 mg, 0.025 mg to 0.25 mg, 0.025 mg to 0.3 mg, 0.025 mg to 0.35 mg, 0.025 mg to 0.4 mg, 0.025 mg to 0.5 mg, 0.05 mg to 0.075 mg, 0.05 mg to 0.1 mg, 0.05 mg to 0.15 mg, 0.05 mg to 0.2 mg, 0.05 mg to 0.25 mg, 0.05 mg to 0.3 mg, 0.05 mg to 0.35 mg, 0.05 mg to 0.4 mg, 0.05 mg to 0.5 mg, 0.075 mg to 0.1 mg, 0.075 mg to 0.15 mg, 0.075 mg to 0.2 mg, 0.075 mg to 0.25 mg, 0.075 mg to 0.3 mg, 0.075 mg to 0.35 mg, 0.075 mg to 0.4 mg, 0.075 mg to 0.5 mg, 0.1 mg to 0.2 mg, 0.1 mg to 0.25 mg, 0.1 mg to 0.3 mg, 0.1 mg to 0.35 mg, 0.1 mg to 0.4 mg, 0.1 mg to 0.5 mg, and doses within 25% of these ranges.

In some instances, the sGCS drug may have an inhaled dose of 0.001 mg, 0.002 mg, 0.003 mg, 0.004 mg, 0.005 mg, 0.006 mg, 0.007 mg, 0.008 mg, 0.009 mg, 0.01 mg, 0.015 mg, 0.02 mg, 0.025 mg, 0.03 mg, 0.035 mg, 0.04 mg, 0.045 mg, 0.05 mg, 0.055 mg, 0.06 mg, 0.065 mg, 0.07 mg, 0.075 mg, 0.08 mg, 0.085 mg, 0.09 mg, 0.095 mg, 0.1 mg, 0.125 mg, 0.15 mg, 0.2 mg, 0.25 mg, 0.3 mg, 0.35 mg, 0.4 mg, 0.45 mg, 0.5 mg, or a dose within 25% of any of these doses.

Vasodilators can be co-administered with each other and with other types of drugs, including bronchodilators. As a non-limiting example, the nominal dose of vardenafil (in base form) for an inhaled PRN therapeutic formulated in a carrier-based formulation and delivered with a capsule-based dry powder inhaler typically ranges from about 0.1 mg to about 2.0 mg, (e.g., between 0.15 and 0.50 mg). In the same formulation, the nominal dose of albuterol (in base form) is between 0.05 mg and 0.3 mg. For example, in a fixed dose combination the dose of vardenafil is 0.2 mg and the dose of albuterol is 0.1 mg. The fill mass is between 12.5 and 25 mg. The emitted dose for a carrier-based composition of vardenafil and albuterol with a capsule-based DPI are typically greater than 70% of the nominal dose (e.g., greater than 80% of the nominal dose).

Aerosol administration provides for significantly lower doses to be administered for a comparable or superior therapeutic effect in dilating pulmonary blood vessels as compared to oral administration. The drug-device combination product of the present invention limits off target delivery of drug to the oropharynx where it is swallowed and able to contribute to systemic side effects. The contribution of gastrointestinal absorption to systemic delivery is expected to be below 15%, e.g., less than 10%, or less than 5%, wherein the contribution of gastrointestinal absorption to systemic delivery is determined in pharmacokinetic studies with oral activated charcoal.

In some instances, the method comprises the use of the high efficiency dry powder inhaler to deliver the inhalable, dry powder composition of the vasodilator at a concentration that causes pulmonary blood vessel dilation of sufficient duration at a much lower systemic drug concentration level than oral dosing, minimizing the risk of hypoxia. In some instances, the drug delivery may be accomplished by a small, portable, passive (powered only by the patient's inhalation effort), and high efficiency dry powder inhaler selectively delivering drug to the lungs to the ventilated areas of the lung at much lower overall dose than oral or IV medications. In PH patients, critically, this means that the inhaled PDE5i drug would be delivered to areas of the lung that are both ventilated and also perfused. By doing so one would be able to better maintain V/Q ratio, as described below, minimizing the risk of hypoxia in these patients, while enhancing the patient's quality of life.

C. Therapeutic Outcomes

Treatment with an inhaled PRN therapeutic is intended to acutely improve exercise tolerance and PH-related symptoms, thereby improving patient quality of life by affording them the opportunity to perform additional activities. The outcomes of PRN methods disclosed herein can be assessed by monitoring indicators of cardiovascular health, measuring a subject's capacity for everyday tasks and exercise (or the level of everyday tasks and exercise), and/or by rating the subject's health-related quality of life.

1. Hemodynamic Measures

Pulmonary hemodynamics are typically measured with an invasive right heart catheterization procedure. In a right-heart catheterization, a pulmonary artery (PA) catheter (also referred to as a Swan-Ganz catheter) is guided to the right side of the heart and passed into the pulmonary artery. Blood flow through the heart (e.g., cardiac output) is measured, as well as the pressure inside the heart (left atrial filling pressure or capillary wedge pressure) and lung arteries (mean pulmonary artery pressure (mPAP)), and the pulmonary vascular resistance is calculated.

The hemodynamic definition of pulmonary arterial hypertension (PAH) is a mean pulmonary artery pressure at rest greater than or equal to 25 mmHg in the presence of a pulmonary capillary wedge pressure less than or equal to 15 mmHg. Pulmonary hemodynamic measurements can be used to assess the outcomes of the methods disclosed herein. In some embodiments, for example, methods for treating PAH are provided wherein a 10% or greater improvement in mean pulmonary arterial pressure (mPAP) is observed within 10 min of inhalation. In some embodiments, a 10% or greater improvement in mPAP is observed within 20 min of inhalation. In some embodiments, a 20% or greater improvement in mPAP is observed within 10 min of inhalation. In some embodiments, a 20% or greater improvement in mPAP is observed within 20 min of inhalation (e.g., within 15 min of inhalation). In some embodiments, these improvements in mPAP are observed over a period of at least 1 hr following administration of the vasodilator (e.g., more than 2 h or more than 3 h).

Cardiac output refers to the amount of blood ejected by the heart in a unit of time, usually expressed in units of liters per minute. Aerobic exercise capacity in PAH patients is mainly limited by cardiac output. The PRN formulations and methods disclosed herein generally provide improvements in cardiac output relative to placebo. In some embodiments, the PRN formulations and methods provide statistically significant improvements in cardiac output relative to placebo in a placebo-controlled clinical study, with a p-value less than 0.05 (e.g., less than 0.01).

Pulmonary vascular resistance (PVR) refers to the resistance to blood flow in the pulmonary circuit, which represents the difference between the mean pulmonary arterial pressure and the left atrial filling pressure (or capillary wedge pressure) divided by the cardiac output. In some embodiments, methods for treating PAH are provided wherein a 10% or greater improvement in mean PVR is observed within 10 min of inhalation. In some embodiments, a 20% or greater improvement in PVR is observed within 20 min of inhalation. In some embodiments, the improvement in PVR is observed over a period of at least 1 hr following administration of the vasodilator (e.g., more than 2 h or more than 3 h).

Systemic vascular resistance (SVR) refers to the resistance to blood flow of the systemic circuit. The PVR:SVR ratio observed upon administration of a particular vasodilator serves as indicator of the vasodilator's selective action on the pulmonary circuit vs. the systemic circuit. In some embodiments, methods for treating PAH are provided wherein a change in the PVR:SVR ratio greater than −10% is observed upon administration of a vasodilator. In some embodiments, the change in PVR:SVR ratio is greater than −20%. In general, no clinically significant changes in systemic blood pressure are observed upon administration of the vasodilator.

2. Exercise Tolerance and Symptoms

A significant advantage of the inhaled PRN therapeutics disclosed herein is that the they are effective in acutely improving exercise tolerance and symptoms, including dyspnea. The PRN compositions and methods disclosed herein provide quantifiable improvements in exercise tolerance and capacity for day-to-day activities. Improved exercise tolerance may be assessed by a variety of endpoints that include improvements in the validated six-minute walk test (6MWT). Alternatively, improvements in the number of steps per day or METS other associated endpoints may be assessed with a wearable device (e.g., an activity monitor).

Acute improvements in exercise tolerance resulting from the administration of a vasodilator may be assessed with serial 6MWT. Under this scenario, subjects are asked to complete a 6MWT. PRN vasodilator or placebo is then administered within 5 min of completing the first 6MWT, and a second 6MWT is initiated within 30 min of the first walk. The PRN formulations and methods described herein generally provide an improvement in the serial 6MWT relative to placebo, as quantitated, for example, by the difference in the distance walked between the two walks between which a dose of vasodilator is administered. In some embodiments, the PRN formulations and methods provide a statistically significant improvement in the serial 6MWT relative to placebo in a placebo-controlled clinical study, with a p-value less than 0.05 (e.g., less than 0.01). In some embodiments, an improvement in exercise tolerance is evidenced by a distance increase of more than 5 meters (e.g., more than 10 meters or more than 15 meters) accomplished during the serial 6MWT as compared to placebo.

As another example, the ActiGraph activity monitor uses a solid-state triaxial accelerometer to collect data in three axes—vertical, anteroposterior, and mediolateral—at a frequency of 30 Hz. All three axes provide activity counts to compute a composite vector magnitude (VM). Data are presented in terms of the average intensity (sedentary, low, moderate, vigorous, or very vigorous) physical activity. PAH patients spend most of their time sedentary and exhibit an average VM activity of about 400 counts/min (Matura, 2016). The PRN formulations and methods disclosed herein generally provide significant improvements in VM counts, as measured by an activity monitor, relative to placebo. In some embodiments, the PRN formulations and methods provide statistically significant improvements in VM counts, as measured by an activity monitor, relative to placebo in a placebo-controlled clinical study, with a p-value less than 0.05 (e.g., less than 0.01).

Dyspnea and other symptoms of PH are complex, multifaceted, and highly personalized sensory experiences, the source and mechanisms of which are not completely understood. PH symptoms are often assessed with the Borg Index, that measures the rating of perceived exertion (RPE) on a Likert-based RPE scale. The Borg Index is especially useful in the assessment of breathlessness, dyspnea, chest pain, and musculoskeletal pain associated with exertion. The PRN formulations and methods disclosed herein generally provide improvements in PH symptoms, as rated by the Borg Index, relative to a placebo. In some embodiments, the PRN formulations and methods disclosed herein provide statistically significant improvements, as rated by the Borg Index, relative to a placebo in a placebo-controlled clinical study, with a p-value less than 0.05 (e.g., less than 0.01).

Heart rate recovery at 1 min (HRR1) is another measure that can be used to assess improvements. HRR1 represents the difference between a subject's heart rate at the sixth minute of the six-minute walk test (6MWT), and at 1 min after completion of the 6MWT. Accordingly, the PRN formulations and methods disclosed herein can also provide improvements in HRR1 relative to placebo. In some embodiments, the PRN formulations and methods provide statistically significant improvements in HRR1 relative to placebo in a placebo-controlled clinical study, with a p-value less than 0.05, (e.g., less than 0.01).

There is evidence that PAH may not only impact the pulmonary arteries and arterioles, but that there may also be obstruction or compression of small airways caused by the perivascular and vascular thickening of small arteries. Alternatively, local inflammatory events may lead to small airway obstruction. Without wishing to be bound by any particular theory, it is believed that small airway obstruction is common to PAH patients (i.e., in up to 80% of subjects), and is more pronounced in severe disease. These features may render the air-vessel space less distensible, and ultimately could be a major component of the dyspnea that PAH patients feel.

Airway obstruction is often assessed via measurement of pressure-volume curves in a pulmonary function test. Mean expiratory flow (MEF) refers to a subject's mean speed of expiration, as measured with a peak flow meter, a small, hand-held device used to monitor the subject's ability to breathe out air. $MEF_{25}$ and $MEF_{50}$ are the mean expiratory flow rates at 25% or 50% of vital capacity (i.e., the greatest volume of air that can be expelled from the lungs after taking the deepest possible breath). Reduced $MEF_{25}$ and $MEF_{50}$ are indicative of a patient having peripheral airway obstruction. The PRN formulations and methods disclosed herein generally provide improvements in $MEF_{25}$ and/or $MEF_{50}$ relative to placebo. In some embodiments, the PRN formulations and methods provide statistically significant improvements in $MEF_{25}$ and/or $MEF_{50}$ relative to placebo in a placebo-controlled clinical study, with a p-value less than 0.05 (e.g., less than 0.01).

Inspiratory capacity (IC) refers to the difference between total lung capacity and functional residual capacity (i.e., the volume of air present in the lungs at the end of expiration), and increases in the presence of an airflow limitation, or dynamic hyperinflation. PAH patients with a mean inspiratory capacity above 89% are predicted to have a significantly improved 5-yr survival (94.1% vs. 75.1%, p=0.036). Accordingly, inspiratory capacity is a marker with prognostic relevance in PAH. The PRN formulations and methods disclosed herein generally provide improvements in inspiratory capacity relative to placebo. In some embodiments, the PRN formulations and methods provide statistically significant improvements in IC relative to placebo in a placebo-controlled clinical study, with a p-value less than 0.05 (e.g., less than 0.01).

There are five principal causes for oxygen deficiency in the blood (i.e., hypoxemia): (1) presence at a high altitude; (2) hypoventilation; (3) shunting; (4) impaired diffusion across the alveolar membrane, and; (5) ventilation-perfusion mismatch. The latter two processes are of potential importance in PH patients. Hypoxemia may contribute to the sensation of dyspnea by disposing the respiratory muscles to fatigue, which is exacerbated by the decrease in respiratory muscle strength observed in these patients.

Reduced diffusing capacity for carbon monoxide (DLCO) is a common abnormality observed in PAH. Reduced DLCO has been shown to correlate with reduced exercise capacity and a higher (i.e., more severe) functional class. Reduced DLCO also reflects a decreased capacity for gas exchange. The PRN formulations and methods disclosed herein generally provide improvements in gas exchange (hypoxemia) as evidenced by reductions in DLCO relative to placebo. In some embodiments, the PRN formulations and methods provide improvements in gas exchange (hypoxemia) as evidenced by statistically significant reductions in DLCO relative to placebo in a placebo-controlled clinical study, with a p-value less than 0.05 (e.g., less than 0.01).

Peripheral airway obstruction in PH patients may lead to ventilation-perfusion mismatch (V/Q mismatch). In this scenario, obstructed areas in the lung are poorly ventilated, yet perfused (i.e., low V/Q), while other regions are perfused and more effectively ventilated (i.e., higher V/Q). This V/Q mismatch leads to hypoxemia because the poorly saturated low V/Q areas have a greater impact on overall oxygen saturation. V/Q mismatch is the most common cause of hypoxemia, and is observed in many diseases, including pneumonia, pulmonary embolism, chronic obstructive pulmonary disease, pulmonary fibrosis, asthma, and pulmonary hypertension. V/Q mismatch can be measured with a ventilation/perfusion scan that involves medical imaging using gamma scintigraphy with medical isotopes to evaluate the circulation of air and blood within a patient's lungs. The PRN formulations and methods disclosed herein generally provide reductions in V/Q mismatch relative to placebo. In some embodiments, the PRN formulations and methods provide statistically significant reductions in V/Q mismatch relative to placebo in a placebo-controlled clinical study, with a p-value less than 0.05 (e.g., less than 0.01).

Hypoxemia may ultimately lead to decreases in systemic oxygen tensions (e.g., in arterial blood). Arterial oxygen tension refers to the partial pressure of oxygen in arterial blood (i.e., $P_aO_2$). $P_aO_2$ is measured in arterial blood following an arterial puncture (e.g., a radial artery or a femoral artery). The PRN formulations and methods disclosed herein generally provide improvements in arterial oxygen tension relative to placebo. In some embodiments, the PRN formulations and methods provide statistically significant improvements in arterial oxygen tension relative to placebo in a placebo-controlled clinical study, with a p-value less than 0.05 (e.g., less than 0.01).

3. Patient-Reported Outcomes

A simple patient reported outcome tool may be utilized that assesses the magnitude of change in how PAH patients feel over time on a 5-point Likert scale. The PRN formulations and methods disclosed herein generally provide improvements in patient satisfaction using a Patient Impression of Change tool (e.g., a satisfaction metric based on a 5-point Likert-type scale) relative to a placebo. In some embodiments, the PRN formulations and methods provide clinically and/or statistically significant improvements in patient satisfaction using a Patient Impression of Change tool (e.g., a satisfaction metric based on a 5-point Likert-type scale) relative to a placebo in a placebo-controlled clinical study, with a p-value less than 0.05 (e.g., less than 0.01).

In some embodiments, the improvement as assessed by the Borg index is observed over a period of at least 1 hr following administration of the vasodilator (e.g., more than 2 h or more than 3 h)

A number of other patient reported outcome (PRO) tools can be used to assess the results of the PRN methods provided herein. In addition to those detailed below, there are a number of respiratory specific measures including SF-36, St. Georges Respiratory Questionnaire (SGRQ) that may have utility, particular in PH patients with underlying respiratory disease.

For example, the PAH-SYMPACT® assessment is a PRO tool that was developed specifically for PAH patients, with questions that address symptoms and the impact of those symptoms. See, McCollister, et al. *Respir Res.* 2016, 17:72. The United States Cambridge Pulmonary Hypertension Outcome Review (CAMPHOR) tool includes three separate subscales designed to assess symptoms, functioning, and quality of life of PH patients. The quality of life portion of the assessment is based on the concept that a patient improves his or her quality of life by improving his or her ability and capacity to satisfy his or her needs. The CAMPHOR quality of life subscale ranges from 0 to 25, with lower scores representing a better quality of life. See, McKenna, et al. *Qual Life Res.* 2006, 15:103. The Minnesota Living With Heart Failure (MLWHF) Questionnaire assesses key physical, emotional, social and mental dimensions of quality of life on a 6-point Likert scale. See, Rector et al. *Am J Cardiol.* 1993, 71:1106).

The Treatment Satisfaction Questionnaire for Medication (TSQM) is a 14-item questionnaire designed as a general measure of treatment satisfaction with medication. See, Regnault, et al. *J Cyst Fibros.* 2012, 11:494. The TSQM questions are answered on a 5- or 7-point Likert-type scale. The test covers four domains, corresponding to distinct aspects related to the satisfaction of patients with their treatment (Effectiveness, Side Effects, Convenience, and Global Satisfaction). A score is obtained on a 0-100 scale for each domain with a higher score corresponding to increased satisfaction. Patients who exhibit higher global satisfaction, generally also exhibit greater adherence to treatment.

The Multidimensional Fatigue Inventory (MFI) is a self-administered instrument containing 20 items that measure five subscales covering the dimensionality of fatigue, general fatigue, physical fatigue, reduced activity, reduced motivation, and mental fatigue. See, Smets, et al. *J Psychosomatic Res.* 1995, 39:315. Each of the subscales contains 4 items. Responses are on a Likert scale ranging from "yes that is true" to no, that is not true". Subjects mark the box that most closely resembles "how they have been feeling lately". Each item is on a scale of 1 to 5. The total subscale ranges from 4 to 20, with a higher score indicating increased fatigue.

In general, the PRN formulations and methods disclosed herein provide improvements using a patient reported outcome tool relative to a placebo. In some embodiments, the PRN formulations and methods provide clinically and/or statistically significant improvements using a patient reported outcome tool relative to a placebo in a placebo-controlled clinical study, with a p-value less than 0.05 (e.g., less than 0.01). In some embodiments, the formulations and methods provide improvements as assessed by one or more tools selected from the PAH-SYMPACT tool, the CAMPHOR tool, the MLWHF questionnaire, the TSQM, and the MFI.

4. Adverse Events

As discussed above, improved lung targeting provided by the PRN methods and formulations of the invention can lead to reductions in adverse events and improved tolerability. Side effects associated with vasodilators such as prostacyclin analogs include, but are not limited to, nausea, flushing, diarrhea, jaw discomfort, musculoskeletal pain, headache, rash, and thrombocytopenia. These adverse events can be particularly pronounced for oral delivery and parenteral delivery. Administration via inhalation can be especially advantageous for more severely affected patients who are unable to manage or tolerate parenteral therapy, which requires an infusion pump and carries the risk of infections and infusion site reactions. For example, inhaled therapy may be indicated for acutely ill patients on systemic therapies, as a means to minimize issues with systemic hypotension. In general, the PRN methods and formulation disclosed herein cause no increase in serious adverse events relative to background therapy. If an increase in total adverse events occurs at all, such increase is generally no more than 20% (e.g., less than 10%) relative to background therapy.

III. Compositions for Regional Lung Targeting

Smooth muscle cells within the pulmonary arteries and arterioles are the therapeutic target for the vasodilators (e.g., ambrisentan, bosentan, epoprostenol, iloprost, riociguat, selexipag, sildenafil, tadalafil, vardenafil, treprostinil) in the context of PAH treatment. The inhaled PRN therapeutics effectively target the pulmonary arteries and provide for regional deposition of drug within the lungs. FIG. 1 is a schematic of blood flow in the cardiovascular system, highlighting the two distinct circuits, i.e., the pulmonary circuit and the systemic circuit. The pulmonary circuit carries deoxygenated blood away from the right atrium and right ventricle of the heart to the lungs via the pulmonary arteries, and returns blood oxygenated in the pulmonary capillaries to the left atrium and left ventricle of the heart. The systemic circuit involves flow of oxygenated blood from the left ventricle via the aorta and its branches to capillaries in the tissues where gas exchange occurs. Deoxygenated blood is then carried back into the right atrium of the heart via the vena cava.

Blood flow within the pulmonary circuit can be further subdivided into pre-capillary and post-capillary. Flow of deoxygenated blood through the pulmonary arteries to the capillaries is defined as being pre-capillary, while oxygenated blood exiting the capillaries into the pulmonary veins is defined as post-capillary. Different forms of pulmonary hypertension are classified based on whether the disease is pre-capillary or post-capillary. The WHO pulmonary hypertension classification system depends primarily on quantitative measures of the mean pulmonary artery pressure (mPAP) and pulmonary wedge pressure (PWP). Patients with pulmonary hypertension have a mPAP≥25 mm Hg. Those with pre-capillary disease (WHO Groups 1, 3, 4 and 5) have a PWP≤15 mm Hg, while those with post-capillary disease (WHO Group 2) have a PWP>15 mm Hg.

Gas exchange occurs in the lungs between the alveoli and capillaries, which are located in the walls of the alveoli. In the alveolus, the epithelial cells lining the air-side and the endothelial cells of the capillaries are each one cell thick. The extracellular basement membrane connecting the two cells (i.e., the interstitium) is also very thin. As such, the distance that blood gases have to diffuse to reach the circulation is very short, and for a small molecule gas like oxygen, this occurs very rapidly. Once oxygen is absorbed into the capillary bed in the lungs, blood flow follows the normal 'post-capillary' path via the pulmonary veins into the left atrium, and eventually into the systemic circuit where gas exchange with tissues occurs. Deoxygenated blood leaves the systemic circuit, and enters the right atrium in the pulmonary circuit, eventually entering the lungs 'pre-capillary' via the pulmonary arteries.

In contrast to low molecular weight respiratory gases where delivery to the alveoli during inspiration is highly efficient, regional deposition of higher molecular weight drugs within the lungs can depend on the aerodynamic particle size distribution of the inhaled particles, the inspiratory flow profile of the patient, and the specific anatomical features of their respiratory tract. In contrast to the situation observed for gas exchange, it is possible to deliver drugs directly into small arteries and arterioles in the pre-capillary circuit via inhalation. While the interstitial space between the bronchiolar epithelium and the arteriole endothelium is much larger than is observed in the alveoli, this does not present a significant barrier for drug delivery to the arteriole.

Delivery to the 'pre-capillary' circuit may be especially important for inhaled vasodilators given their propensity to bind to plasma proteins in the systemic circuit. Indeed, only one in twenty vardenafil molecules present in the systemic circuit is able to bind to the PDE5 enzyme. In contrast, all molecules depositing in the small airways may be available to the pulmonary arteries. Hence, regional targeting of aerosols to the small airways, bronchi and bronchioles, while minimizing to the extent possible, deposition in the upper respiratory tract, large airways and alveoli is desired Targeting to specific regions within the lungs is challenging as a result of the anatomical differences between patients and the impact of lung disease on ventilation within the lungs. Nonetheless, some degree of targeting to the small airways is possible through variations in the aerodynamic particle size distribution.

Aerosols having a mass median aerodynamic diameter (MMAD) of less than 3.5 μm are particularly advantageous for effectively targeting the small bronchi and bronchioles. For example, the MMAD can be less than 3.0 μm, or less than 2.5 μm. Aerosols having an MMAD greater than 1.5 μm are advantageous for limiting deposition in the alveoli and particle exhalation.

One limitation of using MMAD to delineate particles for delivery to the small airways is that it fails to account for the impact of patient inspiratory flow rate on particle deposition in the respiratory tract. Inertial impaction is the principal mechanism driving particle deposition in the respiratory tract. Inertial impaction is dependent on both the aerodynamic diameter ($d_a$) of the particles and the inspiratory flow rate (Q) and is proportional to the inertial impaction parameter, $d_a^2Q$. Pharmaceutical impactors separate particles according to their inertial impaction parameter. While the cutoff diameter for the various stages in the impactor vary with flow rate, the inertial impaction parameter remains constant.

For the purposes of this invention, regional targeting of aerosols to the small airways is linked with the stage grouping on a Next Generation Impactor from stage 4 to filter. This corresponds to a cutoff diameter of 2.8 μm for Q=60 L/min, and more importantly to a $d_a^2Q$ of 467 μm² L/min.

In some instances, the method comprises the use of the high efficiency dry powder inhaler to deliver the inhalable, dry powder composition of the vasodilator with high efficiency to the stage grouping on stage 4-F, wherein the drug-device combination achieves a $d_a^2Q$ less than 467 μm² L/min.

There are several inertia sampling apparatuses that can be used to assess aerosol performance of dry powder formulations. (<601> Aerosols, Nasal Sprays, Metered-Dose Inhalers, and Dry Powder Inhalers Monograph, in USP 29-NF 24 The United States Pharmacopoeia and The National Formulary: The Official Compendia of Standards. 2006, The United States Pharmacopeia Convention, Inc.: Rockville, Md. p. 2617-2636 ("USP <601>").) These instruments classify aerosol particles on the basis of the particles' aerodynamic diameter. The Next Generation Impactor® ("NGI") (Copley Scientific, Shoreview, Minn.) is one such instrument. Each stage of the impactor includes a single or series of nozzles with specific cutoff size. Particles are entrained into the apparatus. Those having sufficient inertia will impact on that particular stage collection plate, while smaller particles with insufficient inertia will remain entrained in the airstream and pass to the next stage where the process is repeated. The aerodynamic size distribution of API can be assessed by collecting the deposited API mass and the ED %, RF %, FPF % and MMAD (μm) can be calculated from the API deposition pattern. The emitted dose fraction (ED (%); Eq. 2) is determined as the percentage powder mass emitted from the initial dosing chamber/capsule relative to the total dose in capsules (nominal dose) (TD). Emitted dose (ED) includes the sum of the API mass left on inhaler device and deposited on the device stages. Fine particle fraction (FPF (%); Eq. 3) is expressed as a percentage of fine particle dose (FPD) below a certain aerodynamic cutoff size to ED. Respirable fraction (RF (%); Eq. 4) is defined as the percentage of FPD to total dose (TD).

$$\text{Emitted dose fraction}(ED(\%)) = \left(\frac{ED}{TD}\right) \times 100\% \quad \text{(Eq. 2)}$$

$$\text{Fine particle fraction}(FPF(\%)) = \left(\frac{FPD}{ED}\right) \times 100\% \quad \text{(Eq. 3)}$$

$$\text{Respirable fraction}(RF(\%)) = \left(\frac{FPD}{TD}\right) \times 100\% \quad \text{(Eq. 4)}$$

In some embodiments, a carrier-based composition of vardenafil for administration with a dry powder inhaler is provided, wherein the fine particle fraction less than 5 μm ($FPF_{<5\ \mu m}$) is greater than 35% (w/w) of the emitted dose of the composition, e.g., greater than 40% (w/w) or greater than 50% (w/w) of the emitted dose of the composition.

In some embodiments, a carrier-based composition containing vardenafil and a force control agent for administration with a dry powder inhaler is provided, wherein the $FPF_{<5\ \mu m}$ is greater than 45% (w/w) of the emitted dose of the composition, e.g., greater than 50% (w/w) or greater than 60% (w/w) of the emitted dose of the composition.

Aerosols having a $FPF_{S4-F}$ of greater than 25% of the emitted dose are advantageous for targeting the small bronchi and bronchioles. For example, the $FPF_{S4-F}$ can be greater than 30% or 35% of the emitted dose. This corresponds to particles with a $d_a^2Q$ of less than about 467 μm² L/min.

In some embodiments, a carrier-based composition containing a vasodilator and a force control agent for administration with a dry powder inhaler is provided, wherein the $FPF_{S4-F}$ is greater than 30% (w/w) of the emitted dose of the composition, e.g., greater than 35% (w/w) or greater than 40% (w/w) of the emitted dose of the composition.

The Q Index is a measure of the flow rate dependence of a pharmaceutical aerosol. It is defined as the difference between the total lung dose measured at a 6 kPa pressure drop and the total lung dose measured at a 1 kPa pressure drop, divided by the higher of the two total lung dose values and multiplied by 100%. In some embodiments, a carrier-based vardenafil composition is provided, wherein the Q Index is less than 45%, e.g., less than 35% or less than 25% or less than 15%.

In some embodiments, a carrier-based composition of vardenafil for administration with a dry powder inhaler is provided, wherein the fine particle fraction less than 3 μm ($FPF_{<3\ \mu m}$) is greater than 25% (w/w) of the emitted dose of the composition, e.g., greater than 35% (w/w) or greater than 40% (w/w) of the emitted dose of the composition.

In some embodiments, a carrier-based composition containing vardenafil and a force control agent for administration with a dry powder inhaler is provided, wherein the $FPF_{<3\ \mu m}$ is greater than 35% (w/w) of the emitted dose of the composition, e.g., greater than 40% (w/w) or greater than 45% (w/w) of the emitted dose of the composition.

In preferred embodiments, carrier-based compositions are used for the delivery of active agents. Carrier-based compositions are adhesive mixtures of micronized drug particles with coarse carrier particles. Other components (e.g., fine lactose particles or force control agents) may be added to control cohesive and/or adhesive forces. Carrier-based compositions provide significant improvements in powder flow properties relative to micronized drug alone, leading to accurate and precise metering of drug into receptacles, and improvements in powder dispersion. Certain carrier-based compositions of vasodilators (e.g., PDE5 inhibitors) administered to the patient with pulmonary hypertension are described in International PCT Appl. No. WO/2015/089105 and U.S. Patent Appl. No. 2016/0317542, both of which are incorporated herein by reference in their entireties for all purposes.

In general, the carrier-based compositions contain micronized vasodilator particles with diameters below 20 µm. In certain embodiments, the Dv50 of the micronized vasodilator particles (e.g., micronized vardenafil) is less than 2.5 µm. For example, the Dv50 can be less than 2 µm or less than 1.5 µm. In some embodiments, the Dv50 of the micronized vasodilator particles ranges from about 0.1 µm to about 1.5 µm. In some embodiments, the Dv50 of the micronized vasodilator particles ranges from about 0.1 µm to about 2 µm. In some embodiments, the Dv50 of the micronized vasodilator particles ranges from about 0.1 µm to about 2.5 µm.

Dry powder compositions may contain a powder mix for inhalation of the active ingredient and a suitable powder base such as mono-, di or poly-saccharides (for example, lactose, mannitol, trehalose, or starch). In certain cases, the powder base may form from about 1% to about 99.9% by weight of the composition. In some embodiments, the powder base constitutes 70% to 99.9% of the total composition weight. In some instances, the powder base may act as a carrier, a diluent that aids in dispensing the active agent, and a fluidizing agent to assist dispersion of the active agent.

In some instances, lactose may be a suitable powder base for use with vasodilator dry powder compositions. In some instances, lactose is a suitable powder base for vasodilator compositions for pulmonary administration because it does not react with the vasodilator. In some cases, vasodilator-lactose blends are chemically stable even though lactose is a reducing sugar that could react via a Maillard chemical reaction with functional groups in the vasodilators (e.g., amine groups in vardenafil). The lactose may be, for example, alpha-lactose monohydrate, anhydrous alpha-lactose, anhydrous beta-lactose, or a blend thereof (for example, 70-80% anhydrous beta-lactose and 20-30% anhydrous alpha-lactose). In some instances, lactose (or other powder base) may be sieved, milled, micronized, or some combination thereof.

In some embodiments, the carrier comprises coarse crystalline lactose. The Dv50 of the coarse lactose particles is typically in the range from 30 to 200 µm, or 50 to 100 µm. In some embodiments, the carrier comprises coarse crystalline lactose monohydrate particles (e.g., RESPITOSE SV003, DFE Pharma) having a Dv50 around 60 µm, a Dv10 around 30 µm, and a Dv90 around 100 µm. In some cases, lactose of different size fractions may be combined in a dry powder composition. For example, the adhesive mixture may also comprise a fine lactose fraction. The fine lactose fraction is defined as the fraction of lactose having a Dv50 of less than 10 µm, with a Dv10 greater than 1 µm, but less than 5 µm, and a Dv90 less than about 40 µm. In some embodiments, the carrier comprises fine crystalline lactose monohydrate particles (e.g., LACTOHALE LH230, DFE Pharma) having a Dv50 below 10 µm, a Dv10 from 1 µm to 3 µm, and a Dv90 less than 30 µm. Particle sizes can be determined by laser diffraction obtaining an equivalent volume diameter. The carrier may contain fine lactose in an amount ranging from about 1% (w/w) to about 30% (w/w) based on the total weight of lactose in the formulation. For example, the carrier may contain fine lactose in an amount ranging from about 3% (w/w) to 15% (w/w), or from about 5% (w/w) to about 15% (w/w), or from about 5% (w/w) to about 9% (w/w), or from about 5% (w/w) to about 8% (w/w), based on the total weight of lactose in the composition (e.g., 7.5% (w/w)).

Fine lactose helps to improve the aerosol performance of inhaled products comprising lactose blends by improving powder dispersion. There have been two mechanisms proposed for the beneficial effect of fine lactose. According to the active sites hypothesis, carrier surfaces have sites with a higher surface energy. This leads to greater adhesion forces for drug at these sites. The addition of fine lactose prior to addition of the drug substance blocks adsorption to these sites, thereby facilitating easier detachment of drug particles during aerosolization. In contrast, the agglomerates hypothesis suggests that the drug and fine lactose adhere to each other, forming agglomerates that are more readily entrained and dispersed on aerosolization.

The disclosed carrier-based dry powder compositions may also include, in addition to the active ingredient and powder base, a further excipient such as a mono-, di or poly-saccharides and their derivatives, calcium stearate or magnesium stearate, leucine and its derivatives, lecithin, human serum albumin, polylysine, and polyarginine. In some embodiments, the carrier-based formulation includes a force control agent. Examples of force control agents include, but are not limited to, magnesium stearate, leucine, trileucine, lecithin, saturated phosphatidylcholines such as dipalmitoylphosphatidylcholine or distearoylphosphatidylcholine. In some instances, if magnesium stearate is present in the composition, it may be present in an amount of about 0.2% to 5%, such as 0.6% to 2% or 0.5% to 1.75%, or 0.6%, 0.75%, 1%, 1.25% or 1.5% w/w, based on the total weight of the composition. In some embodiments, the carrier-based composition comprises magnesium stearate (or another force control agent) in an amount ranging from about 0.1% (w/w) to about 2% (w/w). For example, the carrier-based composition can contain magnesium stearate or another force control agent in an amount ranging from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1% (w/w), or from about 1% (w/w) to about 1.1% (w/w), or from about 1.1% (w/w) to about 1.2% (w/w), or from about 1.2% (w/w) to about 1.3% (w/w), or from about 1.3% (w/w) to about 1.4% (w/w), or from about 1.4% (w/w) to about 1.5% (w/w), or from about 1.5% (w/w) to about 1.6% (w/w), or from about 1.6% (w/w) to about 1.7% (w/w), or from about 1.7% (w/w) to about 1.8% (w/w), or from about 1.8% (w/w) to about 1.9% (w/w), or from about 1.9% (w/w) to about 2% (w/w) based on the total weight of the carrier-based composition. The carrier-based composition can contain magnesium stearate or another force control agent in an amount ranging from about 0.2% (w/w) to about 1.8% (w/w), or from about 0.4% (w/w) to about 1.6% (w/w), or from about 0.6% (w/w) to about 1.4% (w/w), or from about 0.8% (w/w) to about 1.2% (w/w) based on the total weight of the carrier-based composition. The magnesium stearate may have a particle size in the range 1 µm to 50 µm, and more particularly 1 µm to 20 µm. Magnesium stearate can be combined with the other components of the blend by high shear mixing or mechanofusion.

As described above, the carrier-based dry powder compositions may contain a vasodilator co-formulated with one or more additional drugs. One example of a co-formulated, dry powder, inhalable composition comprises 0.1 to 5% (w/w) of a finely micronized (1-3 microns average particle size) PDE5i compound or suitable salt thereof and 0.05-10% finely micronized sGC stimulator compound or suitable salt thereof. In certain embodiments, the composition is a dry powder, inhalable composition of vardenafil plus riociguat. The composition also includes a lactose or other suitable powder base and/or other excipients.

As described above, the carrier-based dry powder compositions may contain a vasodilator co-formulated with a bronchodilator. On example, of a co-formulated carrier-based dry powder, inhalable composition of a vasodilator and bronchodilator comprises 0.5% to 2.0% (w/w) of finely micronized (1-3 mm average particle size) vardenafil hydrochloride with 0.25 to 1.0% (w/w) of finely micronized albuterol or suitable salt thereof. The composition also includes the powder base as described above for carrier-based formulations. For a fill mass of about 25 mg, suitable drug loadings are about 0.8% (w/w) for vardenafil, and 0.4% (w/w) for albuterol.

In some embodiments, the powder fill mass for a carrier-based composition comprising a vasodilator (e.g., vardenafil) and lactose monohydrate (delivered with a portable, capsule-based dry powder inhaler) is between 10 mg and 30 mg (e.g., between 12.5 mg and 25 mg), a mass which is advantageous for accurate and precise filling of formulated powder into capsules.

Typically, a carrier-based composition will comprise vardenafil in an amount ranging from about 0.1% (w/w) to about 10% (w/w), e.g., between 0.5% (w/w) and 3.0% (w/w). The composition can contain vardenafil in an amount ranging from about 0.1% (w/w) to about 0.4% (w/w), or from about 0.4% (w/w) to about 0.8% (w/w), or from about 0.8% (w/w) to about 1.2% (w/w), or from about 1.2% (w/w) to about 1.6% (w/w), or from about 1.6% (w/w) to about 2.0% (w/w), or from about 2.0% (w/w) to about 2.4% (w/w), or from about 2.4% (w/w) to about 2.8% (w/w), or from about 2.8% (w/w) to about 3.2% (w/w), or from about 3.2% (w/w) to about 3.6% (w/w), or from about 3.6% (w/w) to about 4.0% (w/w), or from about 4.0% (w/w) to about 4.4% (w/w), or from about 4.4% (w/w) to about 5% (w/w), or from about 5% (w/w) to about 5.4% (w/w), or from about 5.4% (w/w) to about 5.8% (w/w), or from about 5.8% (w/w) to about 6.2% (w/w), or from about 6.2% (w/w) to about 6.6% (w/w), or from about 6.6% (w/w) to about 7.0% (w/w), or from about 7.0% (w/w) to about 7.4% (w/w), or from about 7.4% (w/w) to about 7.8% (w/w), or from about 7.8% (w/w) to about 8.2% (w/w), or from about 8.2% (w/w) to about 8.6% (w/w), or from about 8.6% (w/w) to about 9.0% (w/w), or from about 9.0% (w/w) to about 9.4% (w/w), or from about 9.4% (w/w) to about 10% (w/w) based on the total weight of the carrier-based composition.

The composition can contain vardenafil in an amount ranging from about 0.1% (w/w) to about 0.2% (w/w), or from about 0.2% (w/w) to about 0.4% (w/w), or from about 0.4% (w/w) to about 0.6% (w/w), or from about 0.6% (w/w) to about 0.8% (w/w), or from about 0.8% (w/w) to about 1% (w/w), or from about 1% (w/w) to about 1.2% (w/w), or from about 1.2% (w/w) to about 1.4% (w/w), or from about 1.4% (w/w) to about 1.6% (w/w), or from about 1.6% (w/w) to about 1.8% (w/w), or from about 1.8% (w/w) to about 2% (w/w), or from about 2% (w/w) to about 2.2% (w/w), or from about 2.2% (w/w) to about 2.4% (w/w), or from about 2.4% (w/w) to about 2.6% (w/w), or from about 2.6% (w/w) to about 2.8% (w/w), or from about 2.8% (w/w) to about 3% (w/w), or from about 3% (w/w) to about 3.2% (w/w), or from about 3.2% (w/w) to about 3.4% (w/w), or from about 3.4% (w/w) to about 3.6% (w/w), or from about 3.6% (w/w) to about 3.8% (w/w), or from about 3.8% (w/w) to about 4% (w/w) based on the total weight of the carrier-based composition. The composition can contain vardenafil in an amount ranging from about 0.4% (w/w) to about 3.0% (w/w), or from about 0.6% (w/w) to about 2.8% (w/w), or from about 0.8% (w/w) to about 2.6% (w/w), or from about 1% (w/w) to about 2.4% (w/w), or from about 1.2% (w/w) to about 2.2% (w/w), or from about 1.4% (w/w) to about 2.0% (w/w), or from about 1.6% (w/w) to about 1.8% (w/w) based on the total weight of the carrier-based composition. One of skill in the art will appreciate that the drug loading will increase by around 1.2-fold when the expressed using the molecular weight of vardenafil hydrochloride trihydrate.

In some embodiments, the carrier-based composition comprises treprostinil (or another prostacyclin analog) in an amount ranging from about 0.1% (w/w) to about 2% (w/w). For example, the carrier-based composition can contain treprostinil or another prostacyclin analog in an amount ranging from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1% (w/w), or from about 1% (w/w) to about 1.1% (w/w), or from about 1.1% (w/w) to about 1.2% (w/w), or from about 1.2% (w/w) to about 1.3% (w/w), or from about 1.3% (w/w) to about 1.4% (w/w), or from about 1.4% (w/w) to about 1.5% (w/w), or from about 1.5% (w/w) to about 1.6% (w/w), or from about 1.6% (w/w) to about 1.7% (w/w), or from about 1.7% (w/w) to about 1.8% (w/w), or from about 1.8% (w/w) to about 1.9% (w/w), or from about 1.9% (w/w) to about 2% (w/w) based on the total weight of the carrier-based composition. The carrier-based composition can contain treprostinil or another prostacyclin analog in an amount ranging from about 0.2% (w/w) to about 1.8% (w/w), or from about 0.4% (w/w) to about 1.6% (w/w), or from about 0.6% (w/w) to about 1.4% (w/w), or from about 0.8% (w/w) to about 1.2% (w/w) based on the total weight of the carrier-based composition.

In some embodiments, the carrier-based composition comprises QCC 374 (or another prostacyclin receptor agonist) in an amount ranging from about 0.1% (w/w) to about 2% (w/w). For example, the carrier-based composition can contain QCC 374 or another prostacyclin receptor agonist in an amount ranging from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1% (w/w), or from about 1% (w/w) to about 1.1% (w/w), or from about 1.1% (w/w) to about 1.2% (w/w), or from about 1.2% (w/w) to about 1.3% (w/w), or from about 1.3% (w/w) to about 1.4% (w/w), or from about 1.4% (w/w) to about 1.5% (w/w), or from about 1.5% (w/w) to about 1.6% (w/w), or from about 1.6% (w/w) to about 1.7% (w/w), or from about 1.7% (w/w) to about 1.8% (w/w), or from about 1.8% (w/w) to about 1.9% (w/w), or from about 1.9% (w/w) to about 2% (w/w) based on the total weight of the carrier-based composition. The carrier-based composition can contain QCC 374 or another prostacyclin receptor agonist in an amount ranging from about 0.2% (w/w) to about 1.8% (w/w), or from about 0.4% (w/w) to about 1.6% (w/w), or from about 0.6% (w/w) to about 1.4% (w/w), or from about 0.8% (w/w) to about 1.2% (w/w) based on the total weight of the carrier-based composition.

In other embodiments, non-carrier based dry powder compositions are contemplated. In these compositions the drug and excipients are intimately associated in an engineered particle. Such compositions may be prepared by spray drying. Spray-drying often results in core-shell particles, where the core of the particle contains the drug and stabilizing excipients including buffers, salts, glass-formers (e.g., trehalose, sucrose, sodium citrate), while the shell is comprised of a hydrophobic excipient (e.g., long-chain saturated phosphatidylcholines, leucine, trileucine, magnesium stearate) that controls the surface morphology, surface energy and as a result the interparticle cohesive forces. Core-shell particles often have low tapped densities, resulting in lower fill masses than is observed in carrier-based compositions. Fill masses for potent drugs like the vasodilators of the present invention, are typically in the range from ca., 1 mg to 10 mg, more typically in the range from 2 to 5 mg. Fill mass selection is driven more by the desire to control the accuracy and precision of the filling process, than by any other parameter. The lower fill mass results in higher drug loadings than are typically observed for carrier-based compositions, by around 5- to 10-fold. The TLD for non-carrier based compositions is typically between 40% (w/w) and 90% (w/w) of the nominal dose, such as between 50% (w/w) and 70% (w/w). The delivered dose is typically greater than 80% (w/w), more often greater than 90% (w/w) of the nominal dose. The tapped density of the compositions may be controlled by controlling the composition of the feedstock, by the use of a blowing agent in emulsion-based feedstocks (e.g., the PulmoSphere™ technology as described in U.S. Pat. No. 6,565,885), and by control of the drying conditions. The tapped density is typically in the range from 0.01 to 0.50 g/cm$^3$, more typically in the range from 0.05 to 0.30 g/cm$^3$. Other drying processes to create low density porous particles, such as spray freeze drying, or the variety of supercritical fluid-based processes are also contemplated. Median geometric sizes of the particles as determined by laser diffraction, are typically in the range from 0.5 µm to 10 µm, more typically in the range from 1 to 5 µm. MMAD values are in the range from 1 to 5 µm, with particles in the range from 1.5 to 2.5 µm preferred for targeting the small airways and pulmonary arteries.

The composition may be packaged in various suitable containers for administration to the patient. For example, the composition may be filled into a capsule. In some instances, the composition is packaged into individual hydroxypropylmethylcellulose (HPMC) capsules, each capsule containing a total dose for administration. These capsules may be packaged and supplied in blister packaging for pulmonary administration by the patient using the easy to use high efficiency dry powder inhaler device such as that previously mentioned above. Use of other dosage forms/packaging such as blister strips or reservoir systems are also contemplated. The compositions can be conveniently prepared and/or packaged in unit dosage form.

Certain embodiments provide a combination therapy product comprising the two (or more) drugs, as described above. The second drug (or drugs) is also provided in as low an efficacious dose as possible, minimizing systemic drug concentration upon administration to the lung and resulting in a minimal amount of drug delivered off target to the mouth and throat where it can be swallowed and enter the systemic circulation by the gastro-intestinal system (off target delivery). By targeting delivery more specifically to the lung and minimizing off target delivery, the overall dose delivered to the patient can be minimized, the local lung concentration of the drug can be maximized, and the concentration of the drug in the systemic circulation can be minimized. In some instances, the lower doses of each component drug delivered in combination via inhalation reduces side effects, lowers systemic toxicities, or both. In some instances, the combination formulations would have synergistic effects in that delivering the drugs in combination may provide greater efficacy than either drug taken separately and would be safer for the patient than taking both drugs orally. In some instances, co-administration of the drugs may result in increased duration of action for one or both of the drugs, thereby reducing the total daily dose or number of doses administered to the subject.

The two (or more) drugs may be co-formulated into a single capsule so as to be inhaled in a single inhalation/puff, or may be formulated into separate capsules (or other dose repositories) and provided to the patient to inhale them in parallel or sequentially. In one example, the drugs may be formulated and packaged separately (such as, for example, packaging each in separate capsules in blister packaging) so that the patient may inhale both doses in parallel in a suitably designed dry powder inhaler or sequentially via a single dose inhaler as described herein or in tandem on blister strips in a multi-dose inhaler. Combination products can be manufactured by separately preparing carrier-based compositions having one type of drug on the carrier particles, and then mixing the separate preparations. Alternatively, combination products can be manufactured by preparing carrier-based compositions having two or more types of drugs on the same carrier particle.

For pressurized metered dose inhalers and smart mist inhalers alternative compositions are contemplated.

For pMDI delivery systems, either solution-based or suspension-based formulations are contemplated. For solution-based formulations the drug is dissolved in the propellant and or mixtures of the propellant and a co-solvent such as ethanol. For the highly potent vasodilators of the present invention, the composition of the solution can be determined without undue experimentation by assessing the phase behavior of various combinations of drug, propellant and co-solvent needed to deliver the required nominal dose.

Alternatively, suspension-based pMDI formulations can be made, wherein the drug is dispersed in the propellant. The engineered particles detailed for the dry powder compositions may be of utility here (e.g., the PulmoSphere™ technology) to aid in stabilizing the drug suspension in the propellant. In a preferred embodiment, co-suspensions of micronized drug and small porous lipid carrier particles are contemplated. Preferred lipid particles comprise a 2:1 molar ratio of distearoylphosphatidylcholine to calcium chloride. The lipid particles are prepared by spray-drying a perfluorooctyl bromide-in-water emulsion. Preferred propellants include, but are not limited to, HFA-134a and HFA-227ea. The concentration of the drug in the propellant will be determined by the required therapeutic dose. For the potent vasodilators of the present invention, the drug loading is about 1 mg/ml to about 20 mg/ml, such as 2 mg/ml to 10 mg/ml.

For soft mist inhalers, aqueous-based solutions are contemplated. The aqueous-based solutions may contain an added co-solvent such as ethanol or propylene glycol to increase the solubility of the drug. These formulations are typically sterile, and may have compositions similar to the current marketed parenteral formulations of vasodilators. For tolerability during oral inhalation, the aqueous solution should have a pH in the range from 2.5 to 9.5, an osmolality in the range from 150 to 350 mOsm/kg. The tonicity can be adjusted with salts such as sodium chloride.

In a related aspect, provided herein is a unit dose package containing vardenafil for use with a dry powder inhaler. In general, the unit dose package contains vardenafil in an amount ranging from 0.1 mg to 3 mg in a suitable container. For example, the vardenafil may be contained in a blister package for pulmonary administration (e.g., a blister package as depicted in FIG. 3). In some embodiments, the unit dose package contains vardenafil in an amount ranging from 0.125 mg to 2.5 mg. In some embodiments, the unit dose package contains vardenafil in an amount ranging from 0.5 mg to 1 mg. In some embodiments, the total fill mass of the unit dose package (e.g., the mass of vardenafil and carrier-based composition) ranges from about 10 mg to about 30 mg (e.g., from about 12.5 mg to about 25 mg). In some embodiments, instructions for use of the unit dose package pro re nata are also included. The instructions may instruct the user to self-administer the vasodilator via inhalation before physical exertion (e.g., from 3-60 minutes before physical activity).

IV. Portable Inhalers

Pulmonary administration provides non-invasive, targeted delivery of vasodilators directly to the site of action in the lungs, thereby enhancing pulmonary selectivity and reducing adverse events related to off-target delivery. Portable aerosol delivery systems are particularly advantageous for PRN administration of vasodilators. For the purposes of this invention, 'portable' inhaler refers to an inhaler that easily fits in a pocket or purse. A portable inhaler with a short administration time may be used discreetly in a public place. The methods and compositions provided herein employ drug delivery devices which are portable, simple, and convenient to use (having no power source requirements, no active agent reconstitution steps, and no cleaning requirements), allowing for short administration times and a low daily treatment burden.

Administration of the compositions disclosed herein can be carried out with various classes of portable inhalers, including dry powder inhalers, pressurized metered dose inhalers, and smart-mist inhalers.

In some instances, a high efficiency dry powder inhaler (DPI) may be used to deliver the vasodilator to the patient. In some instances, the inhaler is one as described in U.S. Pat. Nos. 8,651,104; 8,561,609; U.S. Patent Appl. No. 2013/0213397, U.S. Patent Appl. No. 2015/0246189, U.S. Patent Appl. No. 2013/0340747; and U.S. Patent Appl. No. 2015/0314086, each of which are incorporated herein by reference in their entireties for all purposes. Such inhalers enhance the delivery of dry powder compositions of many drugs and also, in some cases pure micronized drugs, including, for example, vardenafil, a PDE5 inhibitor. In particular this inhaler enhances the $FPF_{S4-F}$, to facilitate efficient delivery of drug to the pulmonary arteries.

In certain aspects, methods for aerosolizing dry powder compositions are provided. As a first step, a carrier-based powder pharmaceutical composition comprising a vasodilator (e.g., PDE5 inhibitor, or a pharmaceutically acceptable salt, hydrate, or ester thereof) is provided. In a second step, an inhaler may be provided, the inhaler comprising a dispersion chamber having an inlet and an outlet, and the dispersion chamber containing an actuator that is movable reciprocatable along a longitudinal axis of the dispersion chamber. The first and second steps may be performed in any order or simultaneously. In a third step, air flow is induced through the outlet channel to cause air and the powder pharmaceutical composition to enter into the dispersion chamber from the inlet, and to cause the actuator to oscillate within the dispersion chamber to assist in dispersing the powder pharmaceutical composition from the outlet for delivery to a subject through the outlet. In some instances, the powdered medicament may be stored within a storage compartment (of the inhaler), and wherein the powder pharmaceutical composition is transferred from the storage compartment, through the inlet and into the dispersion chamber. In certain cases, the inlet may be in fluid communication with an initial chamber, and wherein the powder pharmaceutical composition is received into the initial chamber prior to passing through the inlet and into the dispersion chamber.

In practice, a patient may prime an aerosolization device by puncturing a container holding the formulation (such as a capsule or blister), or the patient may transfer drug from a powder reservoir into the inhalation portion of the device, and then inhale. Inhalation by a patient draws the powder through the inhaler device where powder entrainment results in fluidization, and deagglomeration of powder agglomerates into respirable particles. This approach may be useful for effectively dispersing both binary or ternary carrier-based compositions, as well as formulations comprising engineered particles.

Exemplary devices for use in administering the dry powder composition include dry powder inhalers and metered dose inhalers such as, but not limited to TWISTHALER® (Merck), DISKUS® (GSK), HANDIHALER® (BI), AEROLIZER®, TURBUHALER® (AstraZeneca), FLEXHALER® (Astrazeneca), NEOHALER® (BREEZHALER®) (Novartis), PODHALER® (Novartis), EASYHALER® (Orion), NOVOLIZER® (Meda Pharma), ROTAHALER® (GSK), and others. As known to those skilled in the art, different devices will have different performance characteristics based on the device resistance, deaggregation mechanisms, adhesion of drug to the internal flow channels, and the ability of the patient to coordinate and inhale, among other factors.

In some embodiments, the dry powder compositions may be administered using a dry powder inhaler that comprises a dry powder deagglomerator, also referred to as a powder dispersion mechanism. Exemplary powder dispersion mechanisms are described in U.S. Patent Publication Nos. 2013/0340754 and 2013/0340747, which are incorporated herein by reference in their entirety. In some instances, such powder dispersion mechanisms may comprise a bead positioned within a chamber that is arranged and configured to induce a sudden, rapid, or otherwise abrupt expansion of a flow stream upon entering the chamber. In general, the chamber may be coupled to any form or type of dose containment system or source that supplies powdered active agent into the chamber. Referring now to FIG. 2A, a cross-section of an example tubular body 100 having an inlet 102 and a dispersion chamber 104 is shown according to the principles of the present disclosure. In this example, a fluid (air) flow path of the inlet 102 is defined by a first internal diameter 106, and a fluid (air) flow path of the chamber 104 is defined by a second internal diameter 108. Although shown approximately constant in FIG. 2A, at least one of the first internal diameter 106 and the second internal diameter 108 may vary in dimension as defined with respect to a longitudinal axis L of the tubular body 100. In addition to providing desirable fluid flow characteristics, as discussed further below, these configurable dimensions may be defined such as to provide for a draft angle for injection molding.

Figure 2A:
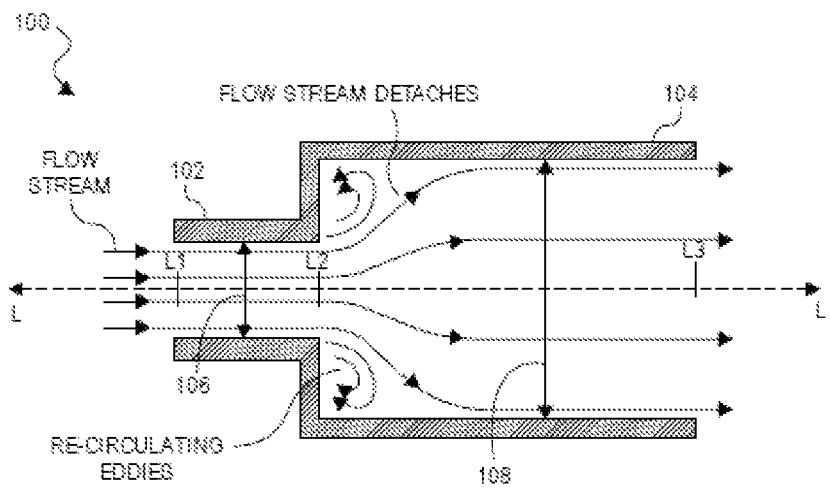
FIG. 2A shows a powder dispersion mechanism according to one embodiment of the present disclosure.
Figure 2B:
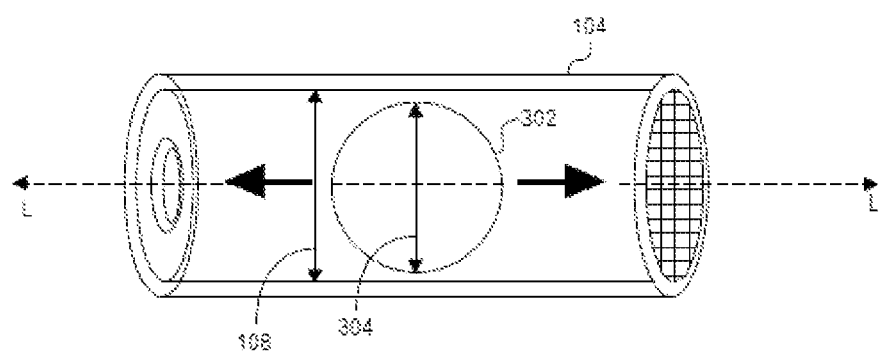
FIG. 2B shows a powder dispersion mechanism according to one embodiment of the present disclosure.

For example, referring now additionally to FIG. 2B, a bead 302 may be positioned within the chamber 104 of the tubular body 100 of FIG. 2A. In this example, the bead 302 may be approximately spherical, at least on the macroscale, and oscillate in a manner similar to that described in U.S. Pat. No. 8,651,104, which is incorporated herein by reference in its entirety. Further, a relationship between the diameter 304 of the bead 302, the first internal diameter 106 of the inlet 102, and the second internal diameter 108 of the chamber 104 may be as described in U.S. Patent Publication Nos. 2013/0340754 and 2013/0340747, which are incorporated herein by reference in their entirety.

In some instances, the powder dispersion mechanism may be coupled to a dry powder inhaler such as a commercially available device. The dispersion mechanism (dispersion chamber) may be adapted to receive an aerosolized powdered active agent from an inlet channel such as described, for example, in U.S. Patent Publication No. 2013/0340754, which is incorporated herein by reference in its entirety. The powder dispersion mechanism (dry powder deagglomerator) may be adapted to receive at least a portion of the aerosolized powdered active agent from the first chamber of the inhaler. The powder dispersion mechanism may include a dispersion chamber that may hold an actuator that is movable within the dispersion chamber along a longitudinal axis. The dry powder inhaler may include an outlet channel through which air and powdered active agent exit the inhaler to be delivered to a subject. A geometry of the inhaler may be such that a flow profile is generated within the dispersion chamber that causes the actuator to oscillate along the longitudinal axis, enabling the oscillating actuator to effectively disperse powdered medicament received in the dispersion chamber for delivery to the patient through the outlet channel.

In one example, the powder dispersion mechanism may have an inlet diameter of about 2.72 mm and an oscillation chamber length and diameter of about 10 mm and about 5.89 mm, respectively. In some instances, the powder dispersion mechanism may include a bead having a diameter within a range of about 0.5 mm to about 15 mm (e.g., 4 mm) in the chamber. In certain instances, a relationship between the diameter 304 of the bead 302, the first internal diameter 106 of the inlet 102, and the second internal diameter 108 of the chamber 104 may be of the form: $d_{bead}^2 \approx (d_{inlet})(d_{chamber})$. In general, this relationship may hold in scenarios where $d_{bead}$ and $d_{inlet}$ and $d_{chamber}$ are of similar order of magnitude. In some instances, the bead may have a density of about 0.9 $mg/mm^3$. In some instances, the bead may be made of polypropylene or a similar material. In some instances, the powder dispersion mechanism can be coupled with a commercial inhaler or other component to form a delivery system for aerosolization of the dry powder compositions. In some cases, the delivery system may work at effectively at different airflow rates and pressure drops within the range of normal physiological inhalation for a subject such as, for example, about 40 to about 60 L/min and about 2 to about 4 kPa.

In certain instances, a dry powder inhaler system may be used to aerosolize and administer the dry powder composition. The dry powder inhaler system may include a receptacle containing an amount of powdered active agent. The dry powder inhaler system may include an inlet channel that is adapted to receive air and powdered active agent from the receptacle. The dry powder inhaler system may include a first chamber that is adapted to receive air and powdered active agent from the inlet channel. A volume of the first chamber may be greater than volume of the inlet channel. The dry powder inhaler system may include a dispersion chamber that is adapted to receive air and powdered medicament from the first chamber. The dispersion chamber may hold an actuator that is movable within the dispersion chamber along a longitudinal axis. The dry powder inhaler system may include an outlet channel through which air and powdered active agent exit the dispersion chamber to be delivered to a patient. A geometry of the system may be such that a flow profile is generated within the system that causes the actuator to oscillate along the longitudinal axis, enabling the oscillating actuator to effectively disperse powdered medicament received in the dispersion chamber for delivery to the patient through the outlet channel.

The use of portable inhalers in conjunction with the methods and compositions disclosed herein provides improvements in patient convenience and treatment satisfaction for inhaled therapies as compared to previously known methods and compositions. For example, the first inhaled therapeutic approved for the treatment of PAH was VENTAVIS® (nebulized iloprost). Iloprost has a very short duration of action (about 30 min), necessitating frequent administration (6 to 9 times daily). VENTAVIS® is currently administered with the I-Neb® Adaptive Aerosol Delivery (AAD®) system (Philips). The I-Neb® is based on a vibrating mesh nebulizer platform coupled with the AAD® system. Software in the AAD® system analyzes the patient's breathing pattern and adapts the pulse of medication for delivery only during patient inspiration. The low dead volume and lack of drug release during expiration leads to an exhaled fraction of less than 10%. The daily treatment burden including the time required to gather the supplies, prepare the nebulizer, administer the dose, and clean the nebulizer was determined clinically, and found to be about two hours/day. A second inhaled prostacyclin (TYVASO®, inhaled treprostinil) was later developed which decreased the number of treatments to four times daily and reduced treatment burden to 39 min/day. Despite the improvements in treatment convenience with TYVASO® there remain reported disadvantages with current inhaled therapies. These include: (a) delivery systems that are cumbersome and time consuming to use; (b) treatment regimens that are cumbersome; (c) irritant effects on airways (cough, bronchospasm, throat irritation), that are described as mild to intractable resulting in discontinuation; (d) prostacyclin-related side effects; (e) treatments that are very costly. All of these factors can have a negative impact on patient adherence to therapy, and ultimately on the effectiveness of the product. These negative impacts can be minimized or avoided altogether by treating PAH with the compositions and methods disclosed herein. Advantages associated with the use of portable inhalers as described herein include, but are not limited to, an administration time of 2 min or less; a daily treatment burden of less than 15 min/day (e.g., less than 10 min/day or less than 5 min/day); and the absence of formal cleaning requirements for the drug delivery advice.

Pressurized metered dose inhalers (pMDI) are another type of portable which can be used in conjunction with the methods and compositions provided herein. pMDI are formulated as either solutions or suspensions in a pharmaceutical-grade propellant such as HFA-134a or HFA-227ea. Co-solvents such as ethanol may be added to increase the solubility of drugs or excipients in the propellant, or to tailor the aerosol performance of the aerosol to CFC-based pMDI. Solution-based pMDIs comprise the drug dissolved in propellant/co-solvent mixtures. Solution-based pMDIs deliver drug with high efficiency to the lungs as compared with suspension-based formulations. Suspension-based formulations contain the drug dispersed in the propellant, often with the aid of surface active agents or polymers. More recently, particle engineering strategies have been advanced relying on particle morphology to control interparticle cohesive forces. For example, the co-suspension technology utilizes mixtures of spray-dried small porous lipid particles and micronized drug to form stable suspensions in propellant. The small porous particles may themselves be formulated with drug, and form stable suspension of drug in propellant.

Solution-based formulations can deliver higher doses of drug to the lungs (up to several mg), provided the solubility in the propellant is sufficient. Advantages of pMDI include their portable, noninvasive delivery, and the ability to contain up to 200 doses in a single device. pMDIs are the most frequently sold portable inhaler in the world. Soft mist inhalers (SMI) utilize microfluidics principles to create liquid sprays comprising liquid droplets of respirable size. SMI are particularly advantageous for delivering water soluble drugs in aqueous droplets, although co-solvents or other solvent-based systems are possible. The principal advantage of SMIs is that they are environmentally-friendly, and deliver a slow-moving spray that has a high delivery efficiency to the lungs. They are available in multi-dose formats. The first-in-class SMI device was the RESPIMAT® (Boehringer Ingelheim). The RESPIMAT was originally developed for the administration of tiotropium in the treatment of breathlessness in chronic obstructive pulmonary disease. New SMIs in development include inhalers from MedSpray (Enschede, Netherlands), Softhale (Hasselt, Belgium), and Pneuma Respiratory (Boone, N.C.).

In a related aspect, provided herein is a kit including a portable inhaler, a vasodilator, and instructions for use of the vasodilator pro re nata. In some embodiments, the portable inhaler is a dry powder inhaler or a metered-dose inhaler. In certain embodiments, the dry powder inhaler is equipped with a dry powder deaglommerator/dispersion mechanism as described above (e.g., a spherical bead positioned to oscillate and disperse a carrier-based composition). In certain embodiments, the inhaler is a dry powder inhaler and the vasodilator is vardenafil formulated as described above. The instructions may instruct the user to self-administer the vasodilator via inhalation before physical exertion (e.g., from 3-60 minutes before an activity such as playing with children, running an errand, or performing an exercise routine).

V. Examples

The following is a non-exhaustive list of patient cases explaining the unique application of an inhaled PDE5i formulation as a PRN therapy for patients with PAH and other forms of PH. One administration of the PDE5i formulation is generally referred to as a "puff" below, referring to an inhalation of the formulation for pulmonary administration. In preferred embodiments, the PDE5i formulation is a vardenafil formulation.

Example 1

A patient with PAH or other form of PH is prescribed multiple puffs per day, PRN, for management of symptoms and exercise limitation due to pulmonary hypertension. Up to 8 puffs per day (each puff at the inhaled doses described above) would likely be a recommended maximum. For example, for a vardenafil formulation administered thusly, the inhaled dose would be $1/10^{th}$ to $1/20^{th}$ of 5 mg b.i.d. for a total of $1/10^{th}$ to $1/20^{th}$ of 10 mg/day (that is 0.05-0.25 mg b.i.d.; total 0.5-1 mg/day).

Example 2

A patient with Scleroderma, a connective tissue disease often associated with PH, may administer the formulation, PRN, when planning to take a walk (e.g., walk to the park to play with his or her children or grandchildren). After dosing with one inhaled dose (puff) of PDE5i formulation, coverage would be expected within 5 to 10 minutes and provide 2 hours or more of symptomatic benefit.

Example 3

A young, pregnant female patient, recently diagnosed with PAH who is characterized as New York Heart Association (NYHA) Functional Class 2, would take a puff or two, depending on the labeled dose of the PDE5i formulation, before setting out on a jog that she would not be able to successfully complete without administration of the PDE5i formulation.

Example 4

A PAH patient with NYHA Functional Class 4, on continuous oxygen therapy, would be able to go to the store or travel to the airport, check in, and complete a flight without carrying a cumbersome oxygen tank because he or she can take periodic puffs of the PDE5i formulation to enhance exercise tolerance and reduce oxygen use.

Example 5

Younger PAH patients would take a puff of the PDE5i formulation to enable them to play a game of soccer, basketball, or baseball with friends.

Example 6

For PH WHO Group 3.1 or Group 3.2 patients, oral PDE5i therapy is not recommended in treatment guidelines (McLaughlin, 2009) for treating the PH component of those diseases because of systemic hypoxia risk. The PDE5i formulation could be used in these patients PRN because local lung delivery of the PDE5i drug would be delivered to areas of the lung that both ventilated and perfused at $1/10^{th}$ to $1/20^{th}$ or lower than the oral dose there would be little or no risk of VQ mismatch induced systemic hypoxia and this would allow more vigorous or more sustained activity, or the same activity with substantial reduction in patient discomfort.

Example 7

Patients with idiopathic pulmonary fibrosis (IPF) without a diagnosis of PH, may benefit from PDE5i formulation administered PRN by increasing exercise capacity, and/or decreasing dyspnea (measured by the Borg Dyspnea Index as described at www.webmd.com/lung/copd/borg-scale-of-perceived-exertion-with-exercise) and/or reducing oxygen use. Their inability to exercise regularly results in deconditioning and further effort limitation. The ability to undertake reasonable effort without disabling respiratory symptoms will improve both function, and sense of wellbeing.

Example 8

Patients with CTEPH who currently cannot take riociguat (the only currently FDA approved drug in this class) or other sGCS medicaments along with PDE5i drugs, would be prescribed either the oral sGCS and an inhaled PDE5i formulation or an inhaled combination therapy consisting of both a sGCS and PDE5i at much lower than normal oral doses. The drugs could be co-formulated or formulated separately for co-administration as described above. The combination of those drugs would be as or more efficacious with lower side effects than either drug taken orally as a monotherapy. Such enhanced efficacy would result in an increased exercise tolerance via 6MWT, lower dyspnea symptoms, and potentially less oxygen use.

Example 9

A female PAH or CTEPH patient who is pregnant and cannot take riociguat or other sGCS medicaments chronically due to the risk of fetal toxicity, would be prescribed an inhaled combination therapy of a very low dose of sGCS plus a low dose of a PDE5i formulation. The law dose of the sGCS combined with the low dose of PDE5i would be as or more efficacious than an oral dose of sGCS and at a dose so low as to not cause a risk of fetal toxicity. Such a combination therapy would be taken by the patient 3-30 minutes before a planned ADL to enable the patient to complete such ADL.

Example 10

This example describes the manufacture of adhesive mixtures of micronized vardenafil hydrochloride and crystalline lactose monohydrate carrier particles.

Two batches of micronized vardenafil hydrochloride trihydrate, USP, EP drug substance were processed in a 4" pilot scale spiral jet mill to reduce the particle size of the drug substance to the respirable range of the present invention. The coarse drug substance as received was forced into the milling chamber by a compressed air stream, through a Venturi tube with a higher pressure (P_vent) and metered into the mill at the desired rate (F-feed). Nitrogen was used as grinding gas and adjusted to the desired pressure (P_grind) to mill the drug particles. The micronized material was characterized for process yield gravimetrically, particle size distribution (PSD) by laser diffraction (Malvern Masersizer) and moisture content by Karl Fischer (KF) analysis. A finer micronized drug substance PSD as evidenced with smaller volume weighted median diameter (Dv50=1.8 μm) and linear interpolated size of the 90th percentile (Dv90=4.5 μm) was obtained using higher Venturi (P_Vent=7.5 bar) and grinding pressures (P_Grind=6 bar) as compared with a batch with a slightly coarser PSD of about 1 μm when using the jet mill operated at lower pressures (ca. P_Vent=5.5 bar and P_Grind=4.5 bar) (Table 1). Both batches had comparable water content after micronization.

TABLE 1

Jet Milling conditions and analytical results for carrier-based vardenafil compositions

| Process Parameter/Characteristics | | | Micronized Drug Substance Batch: Batch 1 | Batch 2 |
|---|---|---|---|---|
| Spiral Jet Mill Process Conditions | | | | |
| P_Vent | | bar | 7.5 | 5.5 |
| P_Grind | | bar | 6 | 4.5 |
| F_Feed | | g/h | 200 | 200 |
| Process yield | | g | 473.89 | 270.77 |
| Physical properties of carrier-based compositions | | | | |
| PSD by Laser diffraction | Dv10 | μm | 0.5 | 0.7 |
| | Dv50 | μm | 1.8 | 2.9 |
| | Dv90 | μm | 4.5 | 5.5 |
| | Span | — | 2.2 | 1.7 |
| Water content by KF | | % w/w | 3.8 | 3.7 |

Twelve formulation blends (six for each micronized drug substance batch) were produced to evaluate the effects of percentage of fine lactose, median diameter (Dv50) of the micronized drug substance and the addition of the force control agent (FCA) magnesium stearate on manufacturability and product performance. LACTOHALE LH230 (DFE Pharma) was used for the fine crystalline lactose monohydrate particles. 150 grams of each blend was formulated to contain 2% drug substance (DS), percent fine lactose ranging from 2.5% to 15% and one formulation containing 5% fine lactose and 1% magnesium stearate (MgSt). The remainder of the formulation composition was made up of RESPITOSE SV003 (DFE Pharma) coarse crystalline lactose monohydrate carrier particles. The composition of each formulation is listed in Table 2.

TABLE 2

Vardenafil Inhalation Powder Blend Formulation

| Lot # | % DS | % fine lactose | % MgSt | Dv50 micronized drug substance (μm) | Batch # |
|---|---|---|---|---|---|
| 4 | 2 | 2.5 | 0 | 1.8 | Batch 1 |
| 5 | | 5 | | | |
| 6 | | 7.5 | | | |
| 7 | | 10 | | | |
| 8 | | 15 | | | |
| 9 | | 5 | 1 | | |
| 10 | 2 | 2.5 | 0 | 2.9 | Batch 2 |
| 11 | | 5 | | | |
| 12 | | 7.5 | | | |
| 13 | | 10 | | | |
| 14 | | 15 | | | |
| 15 | | 5 | 1 | | |

The vardenafil inhalation powder blends were produced in a Diosna high shear mixer (HSM) operated in an environment with monitored relative humidity (RH<40%) and temperature (T<25° C.). The blending procedure for the 12 batches consisted of preparing a pre-blend of the two grades of lactose followed by the addition of the DS. The formulated blend manufacture occurred as follows: Both lactose grades were sieved through a 450 μm sieve. The total amounts of fine and coarse lactose required were weighed and added to a vessel on the HSM and mixed at 450 RPM for 5 minutes in the main impeller and 500 RPM in the chopper. The blended lactose was removed and set aside. The total amount of drug substance required was weighed and sieved. Half the drug substance was combined with ⅓ of the blend of lactose grades in a 0.5 L vessel and mixed for 5 minutes using the HSM operated at 450 RPM in the main impeller and 500 RPM in the chopper. The remaining half of the drug substance was added to the 0.5 L vessel along with the final ⅔ of the blend of lactose grades, and the composition was mixed 5 minutes using the HSM operated at 450 RPM in the main impeller and 500 RPM in the chopper. The formulated blend was transferred into a polyethylene bag and samples were collected for in-process characterization or filled into size #3 HPMC capsules at 10 mg or 30 mg fill mass using a Quantos capsule filler (Mettler Toledo). The blend uniformity (BU) and capsule uniformity (CU) were determined by direct RP-HPLC-UV analysis. Acceptance value (AV) was determined per USP <905>. Quantitation and assay values of sample vardenafil content was achieved by comparison to external standards. Excellent blend uniformity was observed consistently across the various batches.

performance of these lots was studied at 10 mg and 30 mg fill masses, after filling into hypromellose capsules.

Aerosols were administered with a medium resistance (R=0.99 √ cm H$_2$O L$^{-1}$ min) RS01 Model 7 dry powder inhaler (Plastiape, Italy) Aerodynamic particle size distributions were assessed on a Next Generation Impactor at a flow rate of approximately 60 L/min (4 kPa pressure drop). Quantitation of vardenafil content in the aerosol samples was performed using the same Assay method using RP-HPLC-UV described above.

Emitted dose (ED) values varied from 72.3% to 90.6% across the range of formulations, API particle sizes, and fill masses (Table 4, Table 5). Increases in the % fine lactose decreases powder flowability, resulting in decreases in ED. This is especially pronounced for smaller sized drug particles at higher fill masses. Decreasing fill mass also leads to

TABLE 3

Blend uniformity and content uniformity of 2% w/w micronized vardenafil hydrochloride and lactose monohydrate carrier blend formulations and filled capsules (200 μg and 600 μg nominal dose).

| | | | Content Uniformity | | | |
|---|---|---|---|---|---|---|
| | | Blend Uniformity | 10 mg fill mass capsules (nominal dose = 200 μg) | | 30 mg fill mass Capsules (nominal dose = 600 μg) | |
| Lot No. | % Fine Lactose | Assay (% RSD) | Assay (% RSD) | AV | Assay (% RSD) | AV |
| Vardenafil Dv50 = 1.8 μm | | | | | | |
| 4 | 2.5 | 107.1 (2.0) | 100.0 (2.0) | 103.7 (1.0) | 5 | 5 |
| 5 | 5.0 | 100.8 (8.0) | 101.5 (1.7) | 4 (0.8) | 102.3 | 3 |
| 6 | 7.5 | 102.6 (0.8) | 96.8 (1.5) | 5 (0.9) | 100.6 | 2 |
| 7 | 10 | 100.2 (0.8) | 97.3 (1.2) | 4 (0.9) | 97.6 | 3 |
| 8 | 15 | 98.1 (1.5) | 92.8 (1.5) | 9 (1.1) | 98.1 | 3 |
| 9 | 5/1 (FCA) | 97.4 (1.6) | 95.6 (2.4) | 8 (0.6) | 97.9 | 2 |
| Vardenafil Dv50 = 2.9 μm | | | | | | |
| 10 | 2.5 | 101.8 (0.4) | 102.1 (1.2) | 3 (0.8) | 101.7 | 2 |
| 11 | 5.0 | 101.3 (0.5) | 100.3 (1.2) | 3 (0.8) | 101.6 | 2 |
| 12 | 7.5 | 103.1 (0.7) | 107.0 (17.5) | 50 (20.6) | 85.1 | 56 |
| 13 | 10 | 104.5 (0.6) | 96.5 (2.8) | 8 (5.1) | 97.9 | 13 |
| 14 | 15 | 102.2 (1.4) | 102.8 (3.3) | 9 (0.6) | 102.0 | 2 |
| 15 | 5/1 (FCA) | 98.1 (1.2) | 95.6 (2.4) | 9 (1.4) | 96.0 | 6 |

Example 11

A design of experiments (DOE) study was conducted to arrive at a carrier-based dry powder formulation of vardenafil hydrochloride suitable for early clinical development. In this study, two different sizes of micronized vardenafil (Dv50=1.8 μm; Dv50=2.9 μm) were explored. A series of lots were manufactured that differed in the percentage of fine lactose (from 2.5% to 15% w/w). Additional lots comprising 500 w/w lactose fines and 1% w/w magnesium stearate, a force control agent, were also manufactured. The aerosol decreases in ED, as fixed losses of powder due to particle deposition within the device has a greater impact for lower fill masses.

Aerodynamic particle size distributions (APSD) were assessed using the standard 5 μm cutoff diameter, and with a stage grouping from stage 4 to filter (S4-F). At a 60 L/min flow rate this corresponds to a size cutoff of 2.8 μm. Impactors separate particles according to inertial impaction. Particles depositing on S4 and below correspond to an inertial impaction parameter, $d_a^2Q$, less than (467) $\mu m^2$ L/min. Increases in fine particle fraction are observed with increases in the % fine lactose, maximizing at about 7.5% w/w, after which it decreases. Hence, formulations comprising 7.5% w/w fine lactose were chosen for development. Addition of a force control agent lead to further increases in fine particle fraction. Finer drug particles have improved aerosol performance, particularly at higher fill masses. Hence, was advantageous to have micronized drug particles with a Dv50<2 µm. It was further advantageous to provide fill masses in the range around 30 mg to minimize the impact of fixed losses in the device. A fill mass of about 25 mg was particularly advantageous. The addition of a force control agent lead to significant increases in $FPF_{S4-F}$, which is indicative of substantial improvements in deep lung delivery.

("AOS") as described in U.S. Pat. No. 8,651,104 and U.S. Patent Publication Nos. 2013/0340754 and 2013/0340747.

Onbrez Breezhaler drug product (a carrier-based indacaterol maleate formulation) was used for the assessment of the aerosol performance of two capsule-based dry powder inhalers.

The RS01 is a medium resistance capsule-based inhaler. It includes a base unit where the capsule is loaded and prepared for inhalation. The capsule is pierced on either end by depressing two spring loaded buttons that bring forward a metal piercing needle. The needle pierces a single hole on either side of the capsule. Airflow through the capsule seat lifts the capsule and results in precession at high speed

TABLE 4

Aerosol performance of adhesive mixtures of micronized vardenafil hydrochloride and lactose monohydrate carrier particles administered with the medium resistance RS01 DPI (30 mg fill mass; Q = 60 L/min)

| Lot No. | % Fine Lactose | ED (RSD) (%) | $FPD_{<5um}$ (µg) | $FPF_{<5um}$/ED (%) | MMAD (µm) | $FPD_{S4-F}$ (µg) | $FPD_{S4-F}$/ED (%) |
|---|---|---|---|---|---|---|---|
| | | | Vardenafil Dv50 = 1.8 µm | | | | |
| 4 | 2.5 | 90.6 (2.0) | 161.7 | 28.6 | 2.6 | 101.6 | 17.9 |
| 5 | 5.0 | 88.4 (3.3) | 176.2 | 32.2 | 2.5 | 112.2 | 20.5 |
| 6 | 7.5 | 86.1 (2.0) | 186.5 | 35.9 | 2.5 | 122.4 | 23.6 |
| 7 | 10 | 84.8 (1.8) | 185.7 | 35.9 | 2.7 | 111.2 | 21.5 |
| 8 | 15 | 81.4 (2.0) | 174.8 | 36.1 | 3.2 | 90.3 | 18.6 |
| 9 | 5/1 (FCA) | 84.5 (6.4) | 204.9 | 45.1 | 2.0 | 148.3 | 32.7 |
| | | | Vardenafil Dv50 = 2.6 µm | | | | |
| 10 | 2.5 | 81.1 (1.0) | 160.1 | 32.1 | 2.6 | 98.5 | 19.7 |
| 11 | 5.0 | 82.9 (6.9) | 166.5 | 33.0 | 3.0 | 87 | 17.2 |
| 12 | 7.5 | 84.6 (2.6) | 187 | 36.6 | 2.8 | 112.7 | 22.1 |
| 13 | 10 | 82.4 (4.9) | 181.7 | 37.3 | 3.3 | 97.4 | 20.0 |
| 14 | 15 | 78.0 (4.2) | 179.1 | 37.4 | 3.3 | 90.8 | 19.0 |
| 15 | 5/1 (FCA) | 85.8 (2.0) | 199.4 | 41.1 | 2.8 | 119.7 | 24.7 |

TABLE 5

Aerosol performance of adhesive mixtures of micronized vardenafil hydrochloride and lactose monohydrate carrier particles administered with the medium resistance RS01 DPI (10 mg fill mass; Q = 60 L/min)

| Lot No. | % Fine Lactose | ED (RSD) (%) | $FPD_{<5um}$ (µg) | $FPF_{<5um}$/ED (%) | MMAD (µm) | $FPD_{S4-F}$ (µg) | $FPD_{S4-F}$/ED (%) |
|---|---|---|---|---|---|---|---|
| | | | Vardenafil Dv50 = 1.8 µm | | | | |
| 4 | 2.5 | 78.6 (4.2) | 50 | 29.6 | 2.5 | 33.0 | 19.5 |
| 5 | 5.0 | 79.6 (2.7) | 51.1 | 32.0 | 2.3 | 34.4 | 21.5 |
| 6 | 7.5 | 79.4 (6.9) | 55.2 | 30.3 | 2.4 | 37.6 | 23.2 |
| 7 | 10 | 75.5 (2.3) | 54.0 | 35.7 | 2.4 | 35.8 | 23.7 |
| 8 | 15 | 72.3 (4.4) | 52.0 | 37.7 | 2.9 | 30.9 | 22.4 |
| 9 | 5/1 (FCA) | 75.7 (1.7) | 70.1 | 50.0 | 2.0 | 51.4 | 36.7 |
| | | | Vardenafil Dv50 = 2.6 µm | | | | |
| 10 | 2.5 | 75.7 (1.9) | 51.4 | 33.0 | 2.6 | 32.8 | 21.0 |
| 11 | 5.0 | 76.5 (2.4) | 47.9 | 32.1 | 2.6 | 30.5 | 20.3 |
| 12 | 7.5 | 77.2 (3.6) | 53.4 | 33.7 | 3.1 | 27.8 | 17.5 |
| 13 | 10 | 77.1 (4.1) | 51.2 | 35.2 | 2.8 | 30.9 | 21.3 |
| 14 | 15 | 72.7 (3.7) | 56.8 | 38.1 | 3.1 | 31.7 | 21.3 |
| 15 | 5/1 (FCA) | 76.4 (2.1) | 65.9 | 45.3 | 2.5 | 43.6 | 29.9 |

Example 12

This example describes a comparison of the aerosol properties for selected indacaterol maleate adhesive mixtures in using RS01 Monodose Dry Powder Inhaler (Plastiape S.p.A.) ("RS01") alone or modified with AOS™ Dry Powder Inhaler Technology (Respira Therapeutics, Inc.) around its main axis. The resulting centrifugal force within the capsule drives powder fluidization and emission of powder from the capsule. The centrifugal force also leads to collisions between particles and with the capsule and raceway walls leading to dispersion of micronized drug from the carrier. The entrained particles are drawn through a grid into a long mouthpiece that extends like a chimney from the base. Impaction of powder agglomerates with the grid serves to further disperse micronized drug from carrier.

The AOS utilizes the same base as the RS01. The AOS engine is placed within the mouthpiece of the RS01. The AOS engine is comprised of an orifice and a chamber containing an axially oscillating sphere. The design optionally also contains bypass flow to provide control of device resistance. The AOS engine provides additional elements to aid in powder dispersion. The resistance of the AOS device can be modified by the addition of bypass air into the device (AOS+ bypass, below). The AOS device can also be configured so that the bypass air channel is blocked off (AOS− bypass, below).

The aerosol performance of the two devices (RS01, and AOS with and without bypass channel) is compared in Table 6. Significant increases in powder dispersion were observed with the addition of the AOS into the RS01 mouthpiece. This is particularly true for the fine particles depositing on NGI stage 4 to filter, which is deemed the critical fraction of particles for targeting the pulmonary arteries. In this case, improvements in regional targeting provide reductions in nominal dose by 50-70%. The results presented in Table 6 demonstrate that large increases in $FPF_{S4-F}$ are achieved with the addition of the AOS engine. These increases in regional targeting are indicative of significantly improved lung targeting for carrier-based formulations in capsule-based DPIs. This is particular advantageous for minimizing off-target effects with a PRN therapeutic.

TABLE 6

Aerosol performance of carrier-based indacaterol maleate formulations in two capsule-based devices

| Device | Resistance [1] (cm $H_2O^{0.5}$ $L^{-1}$ min) | Q (L/min) [2] | ED (%) | $FPF_{S3-F}$ (% ED) | $\Delta_{S3-F}$ (%) | $EPF_{S4-F}$ (% ED) | $\Delta_{S4-F}$ (%) |
|---|---|---|---|---|---|---|---|
| RS01 (model 7) | 0.09 | 71 | 82 | 39 | — | 22 | — |
| AOS + bypass | 0.14 | 50 | 77 | 49 | +26 | 34 | +55 |
| AOS − bypass | 0.22 | 31 | 75 | 49 | +26 | 39 | +72 |

[1] Resistance values at sea level;
[2] Determinations made at elevation ~5310 ft (1,618 m) in Albuquerque, NM VI. Exemplary Embodiments Exemplary embodiments provided in accordance with the presently disclosed subject matter include, but are not limited to, the claims and the following embodiments:

1. A method of treating pulmonary hypertension, the method comprising administering to a subject in need thereof an effective amount of a vasodilator, wherein the vasodilator is administered to the subject via inhalation pro re nata using a portable inhaler.
2. The method of embodiment 1, wherein the vasodilator is characterized by one or more properties of a log P>0, an oral bioavailability less than 20%, target protein binding in the subject's systemic circuit greater than 90%, and a systemic half-life of under 8 hours.
3. The method of embodiment 1 or embodiment 2, wherein the vasodilator is characterized by a half-life on the target receptor in the pulmonary arteries of greater than 30 minutes.
4. The method of any one of embodiments 1-3, wherein the method acutely improves one or more symptoms of pulmonary hypertension, improves exercise tolerance, improves quality of the life of the subject, or a combination thereof.
5. The method of any one of embodiments 1-4, wherein the portable inhaler is a dry powder inhaler or a metered dose inhaler.
6. The method of any one of embodiments 1-5, wherein the vasodilator is administered at least 3-60 minutes before physical exertion.
7. The method of any one of embodiments 1-6, wherein the vasodilator is administered as a liquid aerosol or a dry powder aerosol.
8. The method of any one of embodiments 1-7, wherein administering the vasodilator comprises targeting the vasodilator to the small airways of the lungs in the subject.
9. The method of any one of embodiments 1-8, wherein the vasodilator is administered as an aerosol having a $FPF_{S4-F}$ of greater than 25% of the emitted dose.
10. The method of any one of embodiments 1-9, wherein the vasodilator is administered as a carrier-based composition comprising micronized vasodilator particles and a powder base.
11. The method of embodiment 10, wherein the Dv50 of the micronized vasodilator particles is less than 2.5 µm.
12. The method of embodiment 10 or embodiment 11, wherein the powder base comprises one or more members selected from the group consisting of lactose, mannitol, trehalose, and starch.
13. The method of any one of embodiments 10-12, wherein the powder base comprises coarse crystalline lactose monohydrate particles.
14. The method of embodiment 13, wherein the Dv50 of the coarse crystalline lactose monohydrate particles is less than or equal to 50 µm.
15. The method of any one of embodiments 10-14, wherein the powder base comprises fine crystalline lactose monohydrate carrier particles.
16. The method of embodiment 15, wherein the Dv50 of the fine crystalline lactose monohydrate carrier particles is less than 10 µm.
17. The method of any of embodiments 13-16, wherein the powder base comprises fine crystalline lactose monohydrate particles and coarse crystalline lactose monohydrate particles.
18. The method of embodiment 17, wherein the ratio of the fine crystalline lactose monohydrate particles to coarse crystalline lactose monohydrate particles ranges from about 5:95 to about 10:90 by weight.
19. The method of any one of embodiments 10-18, wherein the carrier-based composition further comprises a force control agent.
20. The method of embodiment 19, wherein force control agent is selected from the group consisting of calcium stearate, magnesium stearate, leucine, a leucine derivative, lecithin, human serum albumin, polylysine, polyarginine, and combinations thereof.

21. The method of any one of embodiments 10-20, wherein an inhaled dose of about 0.01 mg to about 5 mg of the vasodilator is delivered to the subject upon aerosolization.
22. The method of any one of embodiments 10-21, wherein an inhaled dose of about $1/10^{th}$ to $1/200^{th}$ of a therapeutically effective oral dose of the vasodilator is delivered to the subject upon aerosolization.
23. The method of embodiment 22, wherein an inhaled dose of about $1/10^{th}$ to $1/50^{th}$ of a therapeutically effective oral dose of the vasodilator is delivered to the subject upon aerosolization.
24. The method of embodiment 22, wherein an inhaled dose of about $1/40^{th}$ to $1/200^{th}$ of a therapeutically effective oral dose of the vasodilator is delivered to the subject upon aerosolization.
25. The method of any one of embodiments 1-24, wherein the vasodilator comprises a PDE5 inhibitor, a guanylate cyclase stimulator (sGCS), prostacyclin, a prostacyclin analog, a prostacyclin receptor agonist, or combinations thereof.
26. The method of embodiment 25, wherein the vasodilator is a PDE5 inhibitor.
27. The method of embodiment 26, wherein the PDE5 inhibitor is at least one of vardenafil, sildenafil, tadalafil, avanafil, benzamidenafil, lodenafil, mirodenafil, udenafil, or zaprinast, or a pharmaceutically acceptable salt or ester thereof.
28. The method of embodiment 25, wherein the vasodilator is vardenafil.
29. The method of embodiment 25, wherein the vasodilator is treprostinil.
30. The method of any one of embodiments 10-27, wherein the carrier-based composition comprises about 0.1% to about 10% by weight of a PDE5 inhibitor, or a pharmaceutically acceptable salt, hydrate, or ester thereof, by weight relative to the total weight of the overall carrier-based composition.
31. The method of any one of embodiments 10-30, wherein the carrier-based composition comprises at least about 0.1% to about 10% by weight of vardenafil or a pharmaceutically acceptable salt, hydrate, or ester thereof.
32. The method of any one of embodiments 10-31, wherein the carrier-based composition comprises at least about 0.5% to about 3% by weight of vardenafil or a pharmaceutically acceptable salt, hydrate, or ester thereof.
33. The method of any one of embodiments 1-32, further comprising administering an effective amount of a second drug to the subject.
34. The method of embodiment 33, wherein the second drug is administered to the subject via inhalation pro re nata using a portable inhaler.
35. The method of embodiment 33 or embodiment 34, wherein the second drug is a vasodilator.
36. The method of embodiment 35, wherein the second drug is a soluble guanylate cyclase (sGC) stimulator.
37. The method of embodiment 36, wherein the sGC stimulator is riociguat.
38. The method of embodiment 36 or embodiment 37, wherein an inhaled dose of about $1/10^{th}$ to $1/20^{th}$ of a therapeutically effective oral dose of the sGC stimulator is delivered to the subject upon aerosolization.
39. The method of embodiment 33 or embodiment 34, wherein the second drug is a bronchodilator.
40. The method of any one of embodiments 1-32, wherein the vasodilator is administered as a carrier-based composition by:
providing an inhaler comprising a dispersion chamber having an inlet and an outlet, the dispersion chamber containing an actuator that is movably reciprocatable along a longitudinal axis of the dispersion chamber; and
inducing air flow through the outlet channel to cause air and the carrier-based composition to enter into the dispersion chamber from the inlet, and to cause the actuator to oscillate within the dispersion chamber to assist in dispersing the carrier-based composition from the outlet for delivery to a subject through the outlet.
41. The method of any one of embodiments 33-39, wherein the second drug is administered as a carrier-based composition by:
providing an inhaler comprising a dispersion chamber having an inlet and an outlet, the dispersion chamber containing an actuator that is movably reciprocatable along a longitudinal axis of the dispersion chamber; and
inducing air flow through the outlet channel to cause air and the carrier-based composition to enter into the dispersion chamber from the inlet, and to cause the actuator to oscillate within the dispersion chamber to assist in dispersing the carrier-based composition from the outlet for delivery to a subject through the outlet.
42. The method of any one of embodiments 1-41, wherein the subject has pulmonary arterial hypertension.
43. The method of any one of embodiments 1-42, wherein the subject has interstitial lung disease.
44. The method of any one of embodiments 1-43, wherein the subject has idiopathic pulmonary fibrosis.
45. The method of any one of embodiments 1-44, wherein the physical exertion comprises an activity of daily life.
46. The method of any one of embodiments 1-45, wherein the administration provides 2 hours or more of symptomatic relief.
47. The method of any one of embodiments 1-46, wherein the composition is administered up to 8 times per day.
48. A pharmaceutical carrier-based composition comprising a) about 0.10% to about 10% by weight of a PDE5 inhibitor, or a pharmaceutically acceptable salt or ester thereof, by weight relative to the total weight of the composition, and b) a powder base.
49. The pharmaceutical carrier-based composition of embodiment 48, wherein the PDE5 inhibitor is at least one of vardenafil, sildenafil, tadalafil, avanafil, benzamidenafil, lodenafil, mirodenafil, udenafil, or zaprinast, or a pharmaceutically acceptable salt, hydrate, or ester thereof.
50. The pharmaceutical carrier-based composition of embodiment 48 or 49, wherein the PDE5 inhibitor is vardenafil, or a pharmaceutically acceptable salt, hydrate, or ester thereof.
51. The pharmaceutical carrier-based composition of any one of embodiments 48-50, wherein the PDE5 inhibitor is present in the form of micronized drug particles.
52. The pharmaceutical carrier-based composition of embodiment 51, wherein the Dv50 of the micronized vasodilator particles is less than 2.5 µm.
53. The pharmaceutical carrier-based composition of embodiment 51 or embodiment 52, wherein the powder base comprises one or more members selected from the group consisting of lactose, mannitol, trehalose, and starch.

54. The pharmaceutical carrier-based composition of any one of embodiments 51-53, wherein the powder base comprises coarse crystalline lactose monohydrate particles.
55. The pharmaceutical carrier-based composition of embodiment 54, wherein the Dv50 of the coarse crystalline lactose monohydrate particles is less than or equal to 50 μm.
56. The pharmaceutical carrier-based composition of any one of embodiments 51-55, wherein the powder base comprises fine crystalline lactose monohydrate carrier particles.
57. The pharmaceutical carrier-based composition of embodiment 56, wherein the Dv50 of the fine crystalline lactose monohydrate carrier particles is less than 10 μm.
58. The pharmaceutical carrier-based composition of any of embodiments 54-57, wherein the powder base comprises fine crystalline lactose monohydrate particles and coarse crystalline lactose monohydrate particles.
59. The pharmaceutical carrier-based composition of embodiment 58, wherein the ratio of the fine crystalline lactose monohydrate particles to coarse crystalline lactose monohydrate particles ranges from about 5:95 to about 10:90 by weight.
60. The pharmaceutical carrier-based composition of any one of embodiments 51-59, wherein the carrier-based composition further comprises a force control agent.
61. The pharmaceutical carrier-based composition of embodiment 60, wherein force control agent is selected from the group consisting of calcium stearate, magnesium stearate, leucine, a leucine derivative, lecithin, human serum albumin, polylysine, polyarginine, and combinations thereof.
62. The pharmaceutical carrier-based composition of any one of embodiments 48-61, further comprising a second drug.
63. The pharmaceutical carrier-based composition of embodiment 62, wherein the second drug is a vasodilator.
64. The pharmaceutical carrier-based composition of embodiment 63, wherein the second drug is a soluble guanylate cyclase (sGC) stimulator.
65. The pharmaceutical carrier-based composition of embodiment 64, wherein the sGC stimulator is riociguat.
66. The pharmaceutical carrier-based composition of embodiment 62, wherein the second drug is a bronchodilator.
67. The pharmaceutical carrier-based composition of any one of embodiments 62-66, wherein the PDE5 inhibitor and the second drug are combined in one formulation.
68. The pharmaceutical carrier-based composition of any one of embodiments 62-66, wherein the PDE5 inhibitor and the second drug are separate formulations.
69. A pharmaceutical carrier-based composition of any one of embodiments 48-68 for use in the pro re nata treatment of pulmonary hypertension.
70. The pharmaceutical carrier-based composition of embodiment 69, wherein the composition has a $FPF_{S4\text{-}F}$ of greater than 25% of the pharmaceutical carrier-based composition emitted by a portable inhaler.
71. A kit comprising a portable inhaler, a vasodilator, and instructions for use of the vasodilator pro re nata.
72. The kit of embodiment 71, wherein the portable inhaler is a dry powder inhaler or a metered-dose inhaler.
73. The kit of embodiment 71 or embodiment 72, wherein the vasodilator is selected from the group consisting of PDE5 inhibitor, a guanylate cyclase stimulator (sGCS), prostacyclin, a prostacyclin analog, a prostacyclin receptor agonist, or combinations thereof.
74. The kit of any one of embodiments 71-74, wherein the vasodilator is vardenafil and the portable inhaler is a dry powder inhaler comprising a dry powder deagglomerator.
75. A unit dose package comprising vardenafil in an amount ranging from 0.1 mg to 3 mg and a container.
76. The unit dose package of embodiment 75, wherein the container is a blister package for pulmonary administration.
77. The unit dose package of embodiment 75 or embodiment 76, further comprising instructions for use of the unit dosage package pro re nata.

VII. References

1. Berry, B., et al., Comparison of pharmacokinetics of vardenafil administered using an ultrasonic nebulizer for inhalation vs. a single 10-mg oral tablet. J. Sexual Medicine, published online ahead of print Jul. 28, 2009.
2. Berry, B., et al., Comparison of pharmacokinetics of vardenafil administered using an ultrasonic nebulizer for inhalation vs. a single 10-mg oral tablet, J. Sexual Medicine, Vol. 13, No. 7, pp. 1111-1118, 2016.
3. DeHaan, W. H., Finlay W. H. Predicting extrathoracic deposition from dry powder inhalers. J. Aerosol Sci. 35:309-331, 2004.
4. Delvadia, R., et al., In vitro tests for aerosol deposition II: IVIVCs for different dry powder inhalers in normal adults. J. Aerosol. Med. Pulm. Drug Deliv. 26:138-144, 2013.
5. Finlay, W. H., et al., Choosing 3-D mouth-throat dimensions: a rational merging of medical imaging and aerodynamics. Respir. Drug Deliv. 1:185-194, 2010.
6. Jing, Z-C, et al., Vardenafil treatment for patients with pulmonary arterial hypertension: a multicenter, open-label study, Heart, Vol. 95, pp. 1531-1536, 2009.
7. Jing, Z-C, et al., Vardenafil in pulmonary arterial hypertension: a randomized, double-blind, placebo-controlled study, American Journal of Respiratory and Critical Care Medicine, Vol. 183, No. 12, pp 1723-1729, 2011.
8. McLaughlin, V. V., et al., ACCF/AHA 2009 Expert Consensus Document on Pulmonary Hypertension: A Report of the American College of Cardiology Foundation Task Force on Expert Consensus Documents, J. Amer. College of Cardiology, Vol. 53, No. 17, pp. 1573-1619, 2009.
9. Olsson, B., et al., Validation of a general in vitro approach for prediction of total lung deposition in healthy adults for pharmaceutical inhalation products. J. Aerosol Med. Pulm. Drug Deliv. 26:355-369, 2013.
10. Weers, J. G., et al., In vitro-in vivo correlations observed with indacaterol-based formulations delivered with the Breezhaler®. J. Aerosol Med. Pulm. Drug Deliv. 28:268-280, 2015

The foregoing description of certain aspects and features, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. Certain features that are described in this specification in the context of separate embodiments can also be implemented in combination in a single implementation. Conversely, various features that are described in the context of a single implementation can also be implemented in multiple ways separately or in any suitable sub-combination. Moreover, although features may be described above as acting in certain combinations, one or more features from a combination can in some cases be excised from the combination, and the combination may be directed to a sub-combination or variation of a sub-combination. Thus, particular embodiments have been described. Other embodiments are within the scope of the disclosure.

What is claimed:

1. A method of treating pulmonary arterial hypertension in a subject in need thereof, comprising administering to the subject in need thereof a therapeutically effective amount of micronized vardenafil hydrochloride trihydrate in dry powder form by oral inhalation, pro re nata, delivered by a portable inhaler.

2. The method of claim 1, wherein the portable inhaler is a dry powder inhaler.

3. The method of claim 1, wherein the portable inhaler is a metered dose inhaler.

4. The method of claim 1, wherein the portable inhaler is a capsule-based inhaler.

5. The method of claim 1, wherein the micronized vardenafil hydrochloride trihydrate has a volume weighted median diameter (Dv50) of less than 2.5 μm.

6. The method of claim 1, wherein the micronized vardenafil hydrochloride trihydrate has a volume weighted median diameter (Dv50) of less than 2.0 μm.

7. The method of claim 1, wherein the micronized vardenafil hydrochloride trihydrate has a volume weighted median diameter (Dv50) of less than 1.5 μm.

8. The method of claim 1, wherein the micronized vardenafil hydrochloride trihydrate has a volume weighted median diameter (Dv50) from about 0.1 μm to about 1.5 μm.

9. The method of claim 1, wherein the micronized vardenafil hydrochloride trihydrate has a volume weighted median diameter (Dv50) from about 0.1 μm to about 2.0 μm.

10. The method of claim 1, wherein the micronized vardenafil hydrochloride trihydrate has a volume weighted median diameter (Dv50) from about 0.1 μm to about 2.5 μm.

11. The method of claim 1, wherein the micronized vardenafil hydrochloride trihydrate has a volume weighted median diameter (Dv50) of about 1.8 μm.

12. The method of claim 1, wherein the micronized vardenafil hydrochloride trihydrate has a volume weighted median diameter (Dv50) of about 2.9 μm.

13. The method of claim 4, wherein the powder fill mass of the capsule is from about 10 mg to about 30 mg.

14. The method of claim 4, wherein the powder fill mass of the capsule is from about 12.5 mg to about 25 mg.

15. The method of claim 4, wherein the powder fill mass of the capsule is about 25 mg.

16. The method of claim 4, wherein the powder fill mass of the capsule is about 30 mg.

17. The method of claim 1, wherein the portable inhaler comprises an axially oscillating sphere positioned within a dispersion chamber of the dry powder inhaler.

18. The method of claim 17, wherein the portable inhaler combination achieves a $d_a^2Q$ less than 467 $\mu m^2$ L/minute when the vardenafil hydrochloride trihydrate in dry powder form is deposited on stage 4-F of a Next Generation Impactor.

19. The method of claim 1, wherein the vardenafil hydrochloride trihydrate is administered in a nominal dose from about 0.1 mg to about 2.0 mg of vardenafil.

20. The method of claim 1, wherein the vardenafil hydrochloride trihydrate is administered in a nominal dose from about 0.15 mg to about 0.5 mg of vardenafil.

21. The method of claim 1, wherein the vardenafil hydrochloride trihydrate is administered in a nominal dose from about 0.1 mg to about 3.0 mg of vardenafil.

22. The method of claim 1, wherein the vardenafil hydrochloride trihydrate is administered in a nominal dose from about 0.125 mg to about 2.5 mg of vardenafil.

23. The method of claim 1, wherein the vardenafil hydrochloride trihydrate is administered in a nominal dose from about 0.5 mg to about 1.0 mg of vardenafil.

24. The method of claim 1, wherein the vardenafil hydrochloride trihydrate is administered in a nominal dose of about 0.5 mg vardenafil.

25. The method of claim 1, wherein the vardenafil hydrochloride trihydrate has a $T_{max}$ of 2 minutes or less following administration.

26. The method of claim 1, wherein the vardenafil hydrochloride trihydrate has a half-life of about 2 hours on a PDE5 receptor.

27. The method of claim 1, wherein the vardenafil hydrochloride trihydrate is administered at least 2 to 30 minutes before initiating physical activity.

28. The method of claim 27, wherein the vardenafil hydrochloride trihydrate has a duration of action of at least 1 to 3 hours.

29. The method of claim 1, wherein the daily treatment burden is less than 15 minutes per day.

30. The method of claim 1, wherein the contribution of gastrointestinal absorption to systemic delivery is below 15%.

* * * * *